(12) United States Patent
E et al.

(10) Patent No.: US 12,560,729 B2
(45) Date of Patent: Feb. 24, 2026

(54) SYSTEMS AND METHODS FOR X-RAY IMAGING

(71) Applicant: SHANGHAI UNITED IMAGING HEALTHCARE CO., LTD., Shanghai (CN)

(72) Inventors: Yong E, Shanghai (CN); Jing Yan, Shanghai (CN); Wanli Teng, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 238 days.

(21) Appl. No.: 18/396,838

(22) Filed: Dec. 27, 2023

(65) Prior Publication Data

US 2024/0219591 A1     Jul. 4, 2024

(30) Foreign Application Priority Data

Dec. 28, 2022    (CN) .......................... 202211688406.4

(51) Int. Cl.
| | |
|---|---|
| *G01T 1/29* | (2006.01) |
| *A61B 6/00* | (2024.01) |
| *A61B 6/03* | (2006.01) |
| *G06T 11/00* | (2006.01) |

(52) U.S. Cl.
CPC ............ *G01T 1/2985* (2013.01); *A61B 6/032* (2013.01); *A61B 6/4441* (2013.01); *A61B 6/488* (2013.01); *A61B 6/54* (2013.01); *A61B 6/545* (2013.01); *G06T 11/005* (2013.01); *G06T 2211/444* (2023.08)

(58) Field of Classification Search
CPC ....... A61B 6/032; A61B 6/4441; A61B 6/488; A61B 6/54; A61B 6/545; G06T 11/005
See application file for complete search history.

(56) References Cited

U.S. PATENT DOCUMENTS

| | | | | |
|---|---|---|---|---|
| 9,020,220 B2 * | 4/2015 | Nukui | .................... | A61B 6/542 |
| | | | | 382/128 |
| 2016/0183905 A1 | 6/2016 | Lou et al. | | |
| 2020/0163643 A1 | 5/2020 | Desaute et al. | | |

FOREIGN PATENT DOCUMENTS

| | | |
|---|---|---|
| CN | 103632366 B | 4/2016 |
| CN | 109859276 A | 6/2019 |

* cited by examiner

*Primary Examiner* — Casey Bryant
(74) *Attorney, Agent, or Firm* — METIS IP LLC

(57) ABSTRACT

The present disclosure provides methods and systems for X-ray imaging. The methods may include obtaining pre-scan imaging data relating to a target section of a target subject. The methods may include determining, based on the pre-scan imaging data, a chord length of at least one chord of the target section. The methods may also include determining, based on the chord length of the at least one chord of the target section, exposure parameters to be used by the X-ray imaging device in a target scan of the target subject. The methods may further include reconstructing a target image of the target subject based on scan data collected by the X-ray imaging device in the target scan.

20 Claims, 10 Drawing Sheets

400

100

<u>300</u>

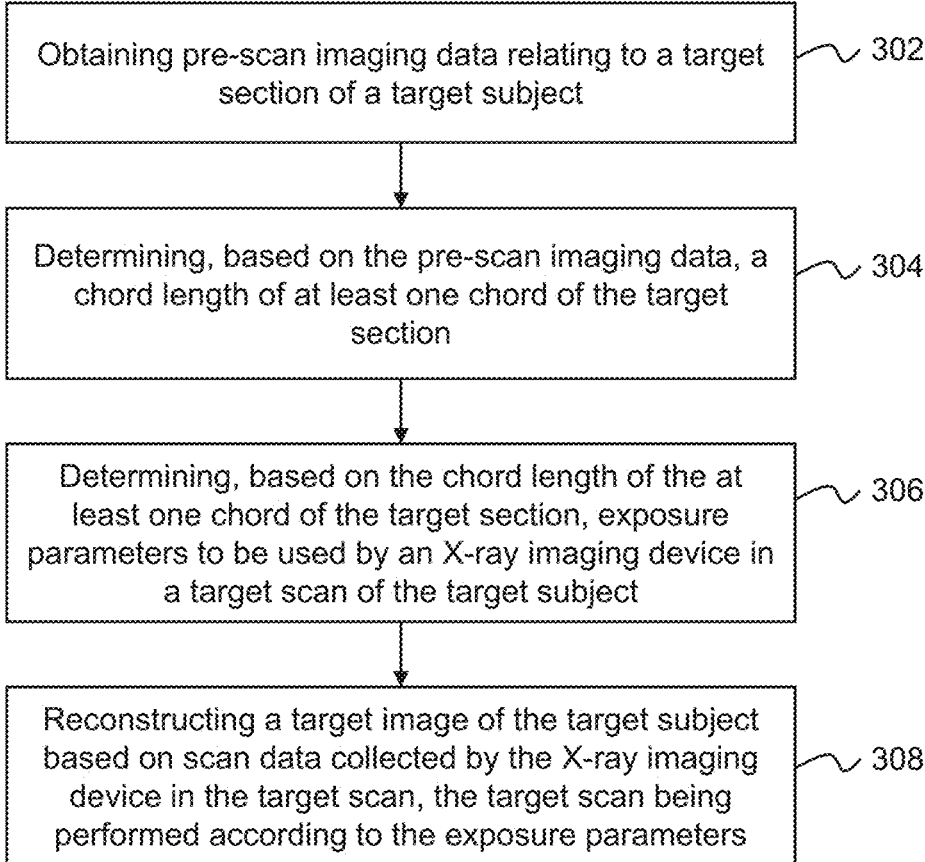

Obtaining pre-scan imaging data relating to a target section of a target subject ~ 302

Determining, based on the pre-scan imaging data, a chord length of at least one chord of the target section ~ 304

Determining, based on the chord length of the at least one chord of the target section, exposure parameters to be used by an X-ray imaging device in a target scan of the target subject ~ 306

Reconstructing a target image of the target subject based on scan data collected by the X-ray imaging device in the target scan, the target scan being performed according to the exposure parameters ~ 308

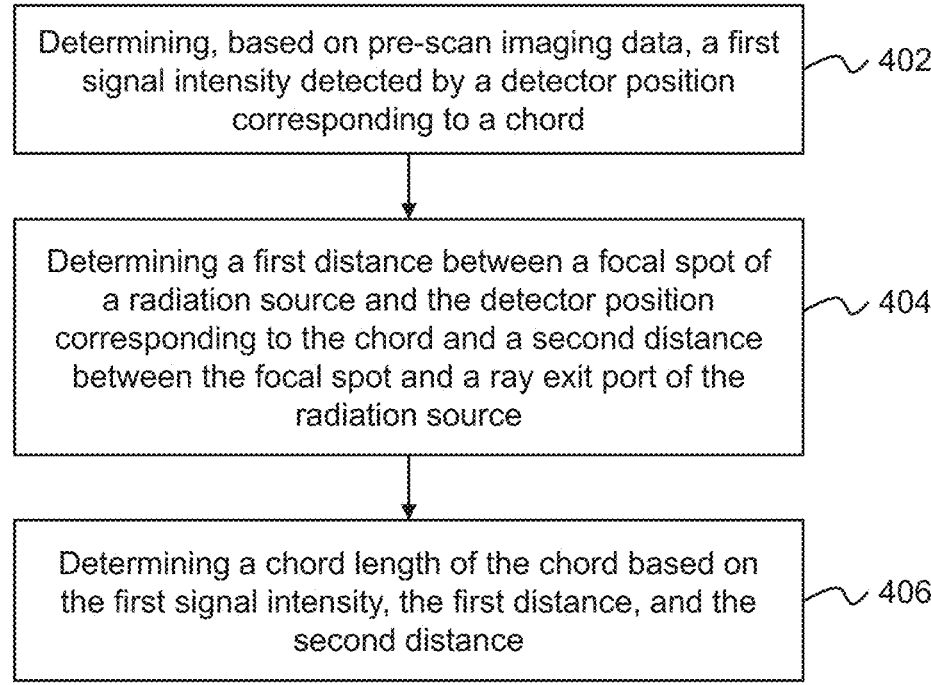

Determining, based on pre-scan imaging data, a first signal intensity detected by a detector position corresponding to a chord ~402

Determining a first distance between a focal spot of a radiation source and the detector position corresponding to the chord and a second distance between the focal spot and a ray exit port of the radiation source ~404

Determining a chord length of the chord based on the first signal intensity, the first distance, and the second distance ~406

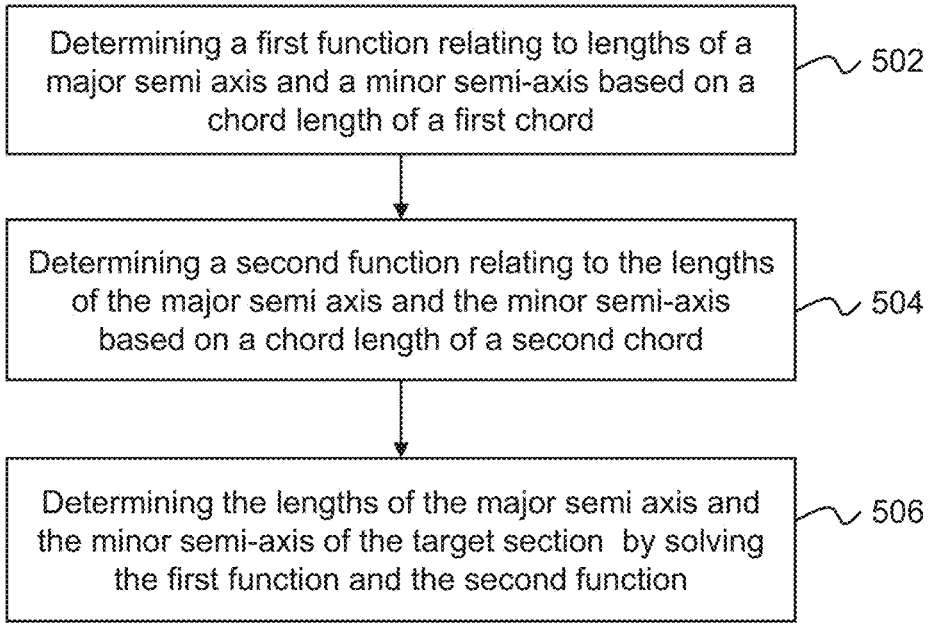

Determining a first function relating to lengths of a major semi axis and a minor semi-axis based on a chord length of a first chord ~502

Determining a second function relating to the lengths of the major semi axis and the minor semi-axis based on a chord length of a second chord ~504

Determining the lengths of the major semi axis and the minor semi-axis of the target section by solving the first function and the second function ~506

SYSTEMS AND METHODS FOR X-RAY IMAGING

CROSS-REFERENCE TO RELATED APPLICATIONS

This application claims priority to Chinese Patent Application No. 202211688406.4, filed on Dec. 28, 2022, the contents of which are incorporated herein by reference.

TECHNICAL FIELD

The present disclosure generally relates to the X-ray imaging field, and more particularly, relates to systems and methods for determining exposure parameters in X-ray imaging.

BACKGROUND

When an X-ray imaging device (e.g., a digital subtraction angiography (DSA) device) scans a subject (e.g., a patient), the subject needs to be irradiated by radiation rays emitted from multiple scanning angles. Since the human body of the patient is not an ideal cylinder, different exposure parameters need to be determined for the multiple scanning angles, so that the multiple scanning angles can correspond to a similar radiation dose on the patient.

Therefore, it is desirable to provide systems and methods for X-ray imaging, which can improve the efficiency and accuracy of exposure parameter determination.

SUMMARY

In an aspect of the present disclosure, a system is provided. The system may include at least one storage device storing a set of instructions for X-ray imaging; and at least one processor configured to communicate with the at least one storage device. When executing the set of instructions, the at least one processor may be configured to direct the system to perform operations. The operations may include obtaining pre-scan imaging data relating to a target section of a target subject. The pre-scan imaging data may be collected by a detector of an X-ray imaging device in a pre-scan, and the target section may be irradiated by pre-scan radiation rays emitted by a radiation source located at a fixed location during the pre-scan. The operations may include determining, based on the pre-scan imaging data, a chord length of at least one chord of the target section. An extension line of each of the at least one chord may pass through a focal spot of the radiation source and a detector position of the detector. The operations may also include determining, based on the chord length of the at least one chord of the target section, exposure parameters to be used by the X-ray imaging device in a target scan of the target subject. The operations may further include reconstructing a target image of the target subject based on scan data collected by the X-ray imaging device in the target scan. The target scan may be performed according to the exposure parameters.

In some embodiments, the determining, based on the pre-scan imaging data, a chord length of at least one chord of the target section may comprise for each of the at least one chord of the target section, determining, based on the pre-scan imaging data, a first signal intensity detected by the detector position corresponding to the chord; determining a first distance between the focal spot and the detector position corresponding to the chord and a second distance between the focal spot and a ray exit port of the radiation source; and determining the chord length of the chord based on the first signal intensity, the first distance, and the second distance.

In some embodiments, the determining the chord length of the chord based on the first signal intensity, the first distance, and the second distance may comprise determining a second signal intensity at the ray exit port of the radiation source; and determining the chord length of the chord based on the first signal intensity, the second signal intensity, the first distance, and the second distance.

In some embodiments, the determining, based on the chord length of the at least one chord of the target section, exposure parameters to be used in a target scan of the target subject may comprise determining, based on the chord length of the at least one chord of the target section, lengths of a major semi-axis and a minor semi-axis of the target section; and determining, based on the lengths of the major semi-axis and the minor semi-axis of the target section, the exposure parameters.

In some embodiments, the at least one chord may include a first chord and a second chord, the first chord may pass through a center of the target section, the second chord may not pass through the center of the target section. The determining, based on the chord length of the at least one chord of the target section, lengths of a major semi-axis and a minor semi-axis of the target section may comprise determining a first function relating to the lengths of the major semi-axis and the minor semi-axis based on the chord length of the first chord; determining a second function relating to the lengths of the major semi-axis and the minor semi-axis based on the chord length of the second chord; and determining the lengths of the major semi-axis and the minor semi-axis of the target section by solving the first function and the second function.

In some embodiments, when the first chord is perpendicular to the detector, the first function may be determined based on the chord length of the first chord and an orientation of the first chord. When the first chord is not perpendicular to the detector, the first function may be determined by: determining a reference chord that is perpendicular to the detector; determining a reference distance between the detector position corresponding to the first chord and a detector position corresponding to the reference chord; and determining the first function based on the chord length of the first chord, the reference distance, and an orientation of the reference chord.

In some embodiments, the whole target section may be within a field of view of the pre-scan, and the determining, based on the chord length of the at least one chord of the target section, lengths of a major semi-axis and a minor semi-axis of the target section may comprise dividing the target section into sub-regions based on the at least one chord; determining areas of the sub-regions based on at least part of the chord length of the at least one chord; and determining the lengths of the major semi-axis and the minor semi-axis of the target section based on the areas of the sub-regions.

In some embodiments, part of the target section may be out of a field of view of the pre-scan, the at least one chord may include a first chord passing through a center of the target section, and the determining, based on the chord length of at least one chord of the target section, lengths of a major semi-axis and a minor semi-axis of the target section may comprise determining a first function relating to the lengths of the major semi-axis and the minor semi-axis based on the chord length of the first chord; determining a third function relating to the lengths of the major semi-axis and the minor semi-axis based on a tangent line of the part of the target section; and determining the lengths of the major semi-axis and the minor semi-axis of the target section by solving the first function and the third function.

In some embodiments, the determining, based on the lengths of the major semi-axis and the minor semi-axis of the target section, the exposure parameters may comprise obtaining reference lengths of the major semi-axis and the minor semi-axis of the target section; determining whether the pre-scan needs to be reperformed based on the lengths and the reference lengths of the major semi-axis and the minor semi-axis of the target section; in response to determining that the pre-scan needs to be reperformed, obtaining second pre-scan imaging data by performing a second pre-scan on the target section; and determining the exposure parameters based on the second pre-scan imaging data.

In another aspect of the present disclosure, a method for X-ray imaging is provided. The method may be implemented on a computing device having at least one processor and at least one storage device. The method may comprise obtaining pre-scan imaging data relating to a target section of a target subject. The pre-scan imaging data may be collected by a detector of an X-ray imaging device in a pre-scan, and the target section may be irradiated by pre-scan radiation rays emitted by a radiation source located at a fixed location during the pre-scan. The method may comprise determining, based on the pre-scan imaging data, a chord length of at least one chord of the target section. An extension line of each of the at least one chord may pass through a focal spot of the radiation source and a detector position of the detector. The method may also comprise determining, based on the chord length of the at least one chord of the target section, exposure parameters to be used by the X-ray imaging device in a target scan of the target subject. The method may further comprise reconstructing a target image of the target subject based on scan data collected by the X-ray imaging device in the target scan. The target scan may be performed according to the exposure parameters.

In still another aspect of the present disclosure, a non-transitory computer readable medium is provided. The non-transitory computer readable medium may comprise executable instructions that, when executed by at least one processor, direct the at least one processor to perform a method. The method may comprise obtaining pre-scan imaging data relating to a target section of a target subject. The pre-scan imaging data may be collected by a detector of an X-ray imaging device in a pre-scan, and the target section may be irradiated by pre-scan radiation rays emitted by a radiation source located at a fixed location during the pre-scan. The method may comprise determining, based on the pre-scan imaging data, a chord length of at least one chord of the target section. An extension line of each of the at least one chord may pass through a focal spot of the radiation source and a detector position of the detector. The method may also comprise determining, based on the chord length of the at least one chord of the target section, exposure parameters to be used by the X-ray imaging device in a target scan of the target subject. The method may further comprise reconstructing a target image of the target subject based on scan data collected by the X-ray imaging device in the target scan. The target scan may be performed according to the exposure parameters.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 3 is a flowchart illustrating an exemplary process for reconstructing a target image according to some embodiments of the present disclosure;

FIG. 4 is a flowchart illustrating an exemplary process for determining a chord length of each of at least one chord of a target section according to some embodiments of the present disclosure;

FIG. 5 is a flowchart illustrating an exemplary process for determining lengths of a major semi-axis and a minor semi-axis of a target section according to some embodiments of the present disclosure;

DETAILED DESCRIPTION

Figure 1:
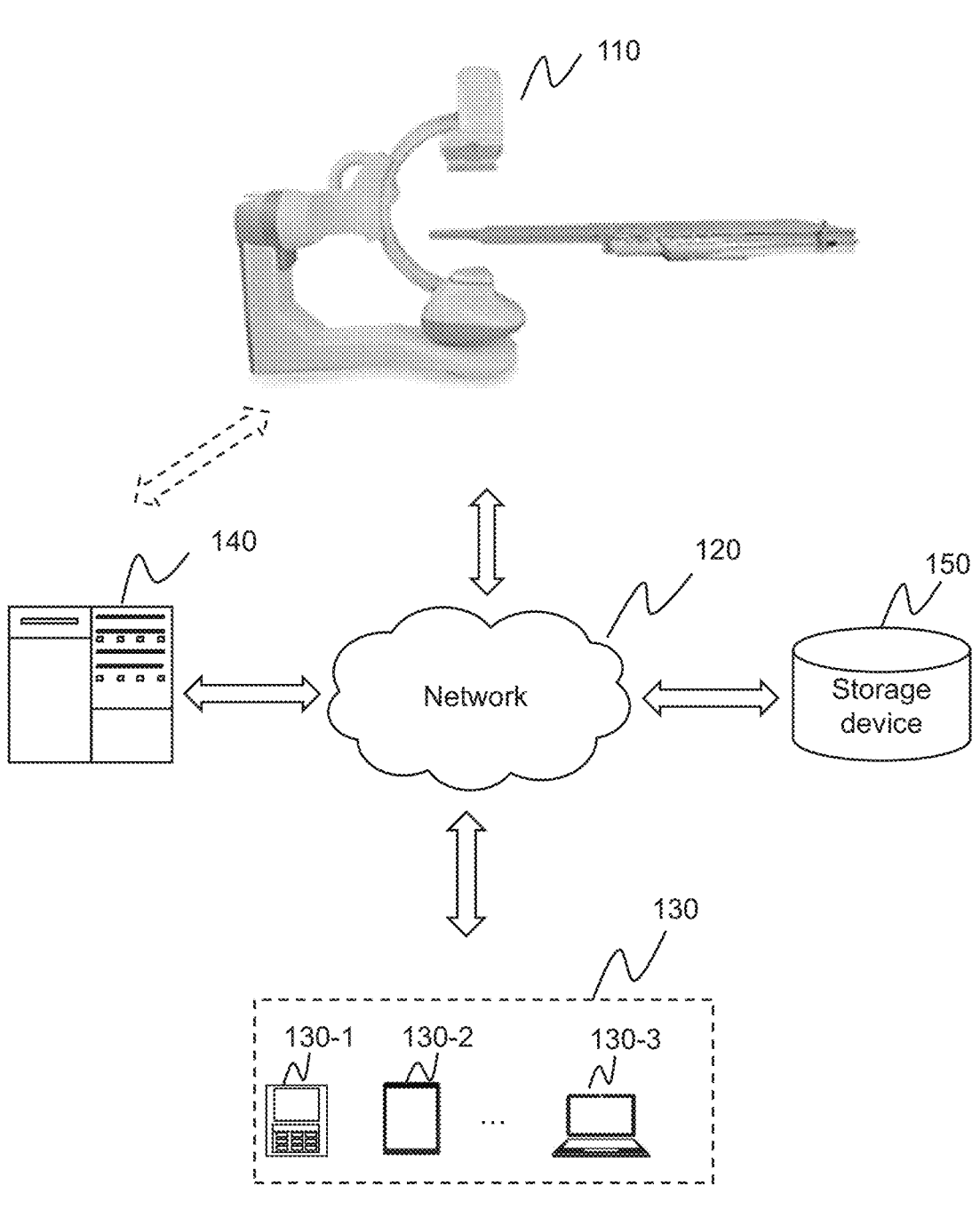
FIG. 1 is a schematic diagram illustrating an exemplary X-ray imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms ("a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The term "pixel" and "voxel" in the present disclosure are used interchangeably to refer to an element in an image. In the present disclosure, the term "image" may refer to a two-dimensional (2D) image, a three-dimensional (3D) image, or a four-dimensional (4D) image (e.g., a time series of 3D images). In some embodiments, the term "image" may refer to an image of a region (e.g., a region of interest (ROI)) of a subject. In some embodiment, the image may be a medical image, an optical image, etc.

In the present disclosure, a representation of a subject (e.g., an object, a patient, or a portion thereof) in an image may be referred to as "subject" for brevity. For instance, a representation of an organ, tissue (e.g., a heart, a liver, a lung), or an ROI in an image may be referred to as the organ, tissue, or ROI, for brevity. Further, an image including a representation of a subject, or a portion thereof, may be referred to as an image of the subject, or a portion thereof, or an image including the subject, or a portion thereof, for brevity. Still further, an operation performed on a representation of a subject, or a portion thereof, in an image may be referred to as an operation performed on the subject, or a portion thereof, for brevity. For instance, a segmentation of a portion of an image including a representation of an ROI from the image may be referred to as a segmentation of the ROI for brevity.

The present disclosure relates to systems and methods for X-ray imaging. The methods may include obtaining pre-scan imaging data relating to a target section of a target subject. The pre-scan imaging data may be collected by a detector of an X-ray imaging device in a pre-scan, and the target section may be irradiated by pre-scan radiation rays emitted by a radiation source located at a fixed location during the pre-scan. The methods may include determining, based on the pre-scan imaging data, a chord length of at least one chord of the target section. An extension line of each of the at least one chord may pass through a focal spot of the radiation source and a detector position of the detector. The methods may also include determining, based on the chord length of the at least one chord of the target section, exposure parameters to be used by the X-ray imaging device in a target scan of the target subject. The methods may further include reconstructing a target image of the target subject based on scan data collected in the target scan. The target scan may be performed according to the exposure parameters.

According to some embodiments of the present disclosure, a pre-scan is performed to irradiate a target section of the target subject using pre-scan radiation rays emitted by a radiation source located at a fixed location, and exposure parameters to be used in a target scan can be determined based on pre-scan imaging data collected in the pre-scan. In other words, the target subject only needs to be irradiated from one scanning angle in the pre-scan for determining the exposure parameters, which can reduce a scanning duration of the pre-scan and a radiation amount on the target subject in the pre-scan. Therefore, damage to the target subject can be reduced, and the efficiency of the exposure parameter determination and/or image reconstruction can be improved.

FIG. 1 is a schematic diagram illustrating an exemplary X-ray imaging system 100 according to some embodiments of the present disclosure. As shown in FIG. 1, the X-ray imaging system 100 may include an X-ray imaging device 110, a network 120, one or more terminals 130, a processing device 140, and a storage device 150. In some embodiments, the X-ray imaging device 110, the processing device 140, the storage device 150, and/or the terminal(s) 130 may be connected to and/or communicate with each other via a wireless connection (e.g., the network 120), a wired connection, or a combination thereof. The connection between the components in the X-ray imaging system 100 may be variable.

The X-ray imaging device 110 may be configured to generate or provide image data by scanning a target subject or at least a portion of the target subject. For example, the X-ray imaging device 110 may acquire pre-scan imaging data relating to a target section of the target subject by performing a pre-scan on the target section of the target subject. In some embodiments, the X-ray imaging device 110 may include a single modality X-ray imaging device. For example, the X-ray imaging device 110 may include a digital subtraction angiography (DSA) device, a computed tomography (CT) device, or the like, or any combination thereof. In some embodiments, the X-ray imaging device 110 may include a multi-modality X-ray imaging device. Exemplary multi-modality X-ray imaging devices may include a digital subtraction angiography-computed tomography (DSA-CT) device, a digital subtraction angiography-magnetic resonance imaging (DSA-MRI) device, etc. The multi-modality scanner may perform multi-modality imaging simultaneously or in sequence. It should be noted that the X-ray imaging device described below is merely provided for illustration purposes, and not intended to limit the scope of the present disclosure.

The target subject may include patients or other experimental subjects (e.g., experimental mice or other animals). In some embodiments, the target subject may be a patient or a specific portion, organ, and/or tissue of the patient. For example, the target subject may include the head, the neck, the thorax, the heart, the stomach, a blood vessel, soft tissue, a tumor, nodules, or the like, or any combination thereof. As another example, the target subject may include a region of interest (ROI), such as a tumor, a node, etc., of the patient. In some embodiments, the target subject may be non-biological. For example, the target subject may include a phantom, a man-made object, etc. The terms "object" and "subject" are used interchangeably in the present disclosure.

The network 120 may include any suitable network that can facilitate the exchange of information and/or data for the X-ray imaging system 100. In some embodiments, one or more components (e.g., the X-ray imaging device 110, the terminal(s) 130, the processing device 140, the storage device 150, etc.) of the X-ray imaging system 100 may communicate information and/or data with one or more other components of the X-ray imaging system 100 via the network 120. In some embodiments, the network 120 may include one or more network access points.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the terminal(s) 130 may be part of the processing device 140.

The processing device 140 may process data and/or information obtained from one or more components (the X-ray imaging device 110, the terminal(s) 130, and/or the storage device 150) of the X-ray imaging system 100. For example, the processing device 140 may obtain the pre-scan imaging data relating to the target section of the target subject. As another example, the processing device 140 may determine a chord length of at least one chord of the target section based on the pre-scan imaging data, and determine exposure parameters to be used in a target scan of the target subject based on the chord length of the at least one chord of the target section. As still another example, the processing device 140 may reconstruct a target image of the target subject based on scan data collected in the target scan. In some embodiments, the processing device 140 may be a single server or a server group. The server group may be centralized or distributed. In some embodiments, the processing device 140 may be local or remote. In some embodiments, the processing device 140 may be implemented on a cloud platform. Exemplary cloud platforms may include a private cloud, a public cloud, a hybrid cloud, a community cloud, a distributed cloud, an inter-cloud, a multi-cloud, or the like, or any combination thereof.

In some embodiments, the processing device 140 may be implemented by a computing device. For example, the computing device may include a processor, a storage, an input/output (I/O), and a communication port. In some embodiments, the processing device 140, or a portion of the processing device 140 may be implemented by a portion of the terminal 130.

The storage device 150 may store data/information (e.g., the pre-scan imaging data, the chord length of the at least one chord of the target section, the exposure parameters, the target image, etc.) obtained from the X-ray imaging device 110, the terminal(s) 130, and/or any other component of the X-ray imaging system 100. In some embodiments, the storage device 150 may include a mass storage, a removable storage, a volatile read-and-write memory, a read-only memory (ROM), or the like, or any combination thereof. In some embodiments, the storage device 150 may store one or more programs and/or instructions to perform exemplary methods described in the present disclosure.

In some embodiments, the X-ray imaging system 100 may include one or more additional components and/or one or more components of the X-ray imaging system 100 described above may be omitted. Additionally or alternatively, two or more components of the X-ray imaging system 100 may be integrated into a single component. A component of the X-ray imaging system 100 may be implemented on two or more sub-components.

Figure 2:
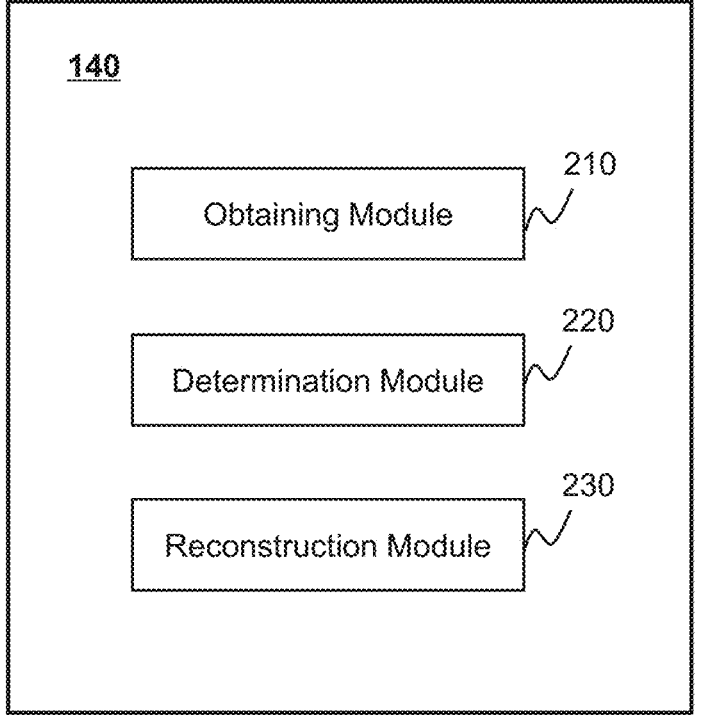
FIG. 2 is a block diagram illustrating an exemplary processing device according to some embodiments of the present disclosure.

FIG. 2 is a block diagram illustrating an exemplary processing device 140 according to some embodiments of the present disclosure. In some embodiments, the processing device 140 may be in communication with a computer-readable storage medium (e.g., the storage device 150 illustrated in FIG. 1) and execute instructions stored in the computer-readable storage medium. The processing device 140 may include an obtaining module 210, a determination module 220, and a reconstruction module 230.

The obtaining module 210 may be configured to obtain pre-scan imaging data relating to a target section of a target subject. The target section of the target subject refers to an intersecting surface between the target subject and a preset plane. The pre-scan imaging data refers to image data (e.g., a 2D image) collected in a pre-scan that is performed before a target scan. In some embodiments, the pre-scan imaging data may be collected by a detector of an X-ray imaging device in the pre-scan. More descriptions regarding the obtaining the pre-scan imaging data may be found elsewhere in the present disclosure. See, e.g., operation 302 and relevant descriptions thereof.

The determination module 220 may be configured to determine, based on the pre-scan imaging data, a chord length of at least one chord of the target section. In some embodiments, an extension line of each of the at least one chord may pass through a focal spot of the radiation source and a detector position of the detector. More descriptions regarding the determination of the chord length of the at least one chord of the target section may be found elsewhere in the present disclosure. See, e.g., operation 304 and relevant descriptions thereof.

The determination module 220 may be further configured to determine, based on the chord length of the at least one chord of the target section, exposure parameters to be used by the X-ray imaging device in the target scan of the target subject. For example, the exposure parameters may include a tube voltage, a tube current, a scanning duration, a scanning angle range, a field of view, or the like, or any combination thereof. More descriptions regarding the determination of the exposure parameters may be found elsewhere in the present disclosure. See, e.g., operation 306 and relevant descriptions thereof.

The reconstruction module 230 may be configured to reconstruct a target image of the target subject based on scan data collected by the X-ray imaging device in the target scan. The target scan may be performed according to the exposure parameters. The target image refers to an image used for diagnosis and/or treatment. More descriptions regarding the reconstruction of the target image may be found elsewhere in the present disclosure. See, e.g., operation 308 and relevant descriptions thereof.

In some embodiments, the processing device 140 may include one or more other modules, one or more modules mentioned above can be omitted. For example, the processing device 140 may include a storage module to store data generated by the modules in the processing device 140. In some embodiments, any two of the modules may be combined as a single module, and any one of the modules may be divided into two or more units.

FIG. 3 is a flowchart illustrating an exemplary process for reconstructing a target image according to some embodiments of the present disclosure. Process 300 may be implemented in the X-ray imaging system 100 illustrated in FIG. 1. For example, the process 300 may be stored in the storage device 150 in the form of instructions (e.g., an application), and invoked and/or executed by the processing device 140.

Before an X-ray imaging device (e.g., the X-ray imaging device 110) performs a target scan on a target subject, exposure parameters to be used in the target scan need to be determined. For example, for a DSA device having a cone beam computed tomography (CBCT) function, the DSA device may rotate around the target subject to scan the target subject from different scanning angles in the target scan, and exposure parameters need to be determined for each scanning angle of the target scan.

Conventionally, a pre-scan is performed to collect pre-scan data of the target subject from both the front and the side of the target subject. Alternatively, a plurality of image frames (e.g., 5, 6, etc., image frames) need be collected by performing the pre-scan within a certain scanning range. However, since the pre-scan is performed from multiple scanning angles, the target subject is subjected to overmuch radiation dose in the pre-scan.

Therefore, in order to reduce the radiation dose to the target subject in the pre-scan without affecting the determination of the exposure parameters, the process 300 may be performed.

In 302, the processing device 140 (e.g., the obtaining module 210) may obtain pre-scan imaging data relating to a target section of a target subject.

The target section of the target subject refers to an intersecting surface between the target subject and a preset plane. For example, the preset plane may pass through the target subject, and the intersecting surface between the target subject and the preset plane may be determined as the target section of the target subject. In some embodiments, the preset plane may be determined based on a system default setting or set manually by a user (e.g., a technician, a doctor, a physicist). For example, the target section may include a cross section, a coronal section, a sagittal section, or any section along the preset direction.

The pre-scan imaging data refers to image data (e.g., a 2D image) collected in a pre-scan that is performed before a target scan. The pre-scan imaging data may be used to determine exposure parameters to be used in the target scan of the target subject. As used herein, both the pre-scan and the target scan are X-ray scans.

In some embodiments, the pre-scan imaging data may be collected by a detector of an X-ray imaging device in the pre-scan. For example, the target section may be irradiated by pre-scan radiation rays emitted by a radiation source (e.g., a radiation source of the X-ray imaging device 110) located at a fixed location during the pre-scan, and a detector (e.g., a detector of the X-ray imaging device 110) may detect attenuated pre-scan radiation rays emitted from the target subject (e.g., the target section of the target subject). The pre-scan imaging data may be generated based on the attenuated pre-scan radiation rays. As used herein, the radiation source refers to a source emitting radiation rays (e.g., the pre-scan radiation rays), and the pre-scan radiation rays refer to radiation rays emitted in the pre-scan. For example, the radiation source may include a three-dimensional (3D) cone beam radiation source, a two-dimensional (2D) fan-beam radiation source, etc. In some embodiments, the pre-scan radiation rays may have a 3D shape that can pass through the target section and cover a portion of the target subject around the target section.

In some embodiments, the processing device 140 may obtain pre-scan parameters of the radiation source, and direct the radiation source to emit the pre-scan radiation rays. Exemplary pre-scan parameters may include the fixed location, a tube voltage, a tube current, a scanning intensity, a scanning duration, a scanning angle range, a field of view, or the like, or any combination thereof.

The fixed location refers to a location where the radiation source is located in the pre-scan. The radiation source may remain at the fixed location and scan the target section from one fixed scanning angle during the pre-scan. In some embodiments, the fixed location may be determined based on the system default setting or set manually by the user. For example, the fixed location may correspond to a scanning angle within the scanning angle range of the target scan. Merely by way of example, if the scanning angle corresponding to an initial location of the radiation source is within the scanning angle range, the initial location may be determined as the fixed location. The initial location refers to a location of the radiation source once the target subject is positioned on the scanning bed. As another example, a location corresponding to the starting scanning angle of the scanning angle range of the target scan may be determined as the fixed location.

In some embodiments, the fixed location may be a suitable position for the radiation source to irradiate the target section, which is determined based on the position of the target section with respect to the target subject and the position of the X-ray imaging device. In some embodiments, the fixed location may be determined empirically. For example, the fixed location may be an optimal location determined based on tests and/or calculations.

Figure 6:
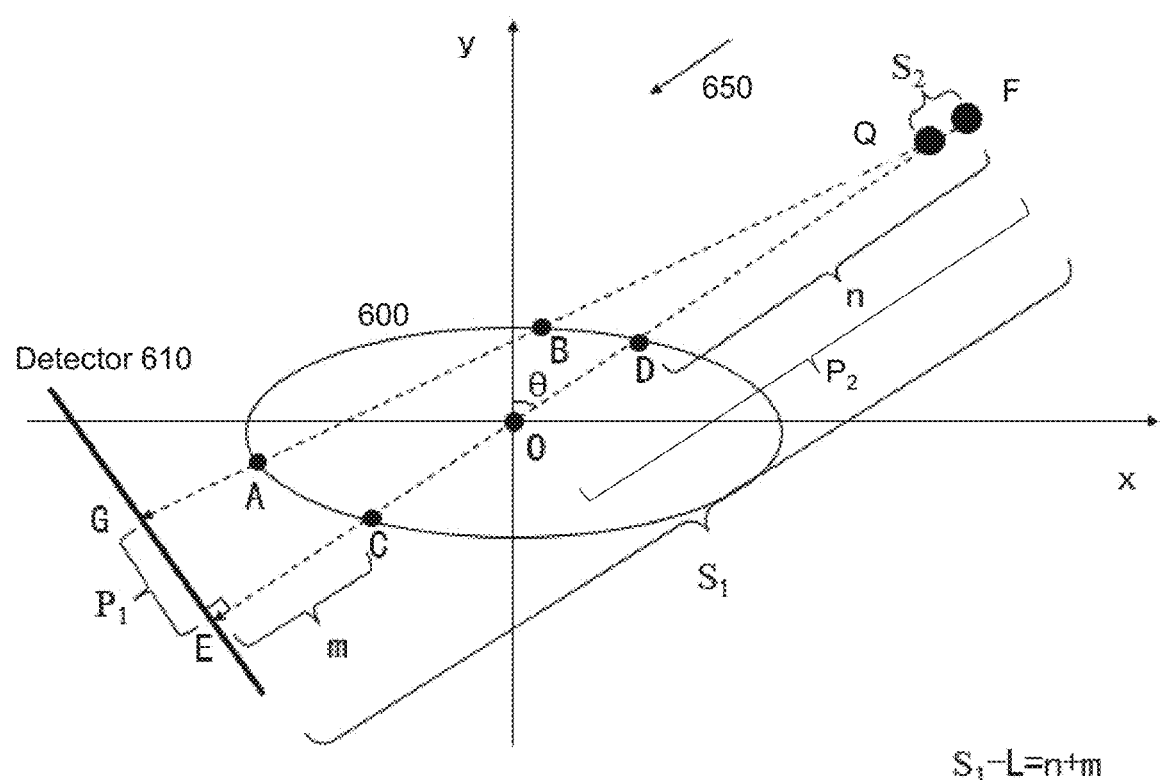
FIG. 6 is a schematic diagram illustrating an exemplary target section of Example 1 according to some embodiments of the present disclosure.

Merely by way of example, as shown in FIG. 6, pre-scan radiation rays (represented as dotted lines) are emitted by a radiation source located at a fixed location during a pre-scan, the pre-scan radiation rays and a target section 600 are located in a same plane (e.g., a plane of a coordinate system xoy), and an extension line of a connection line between a focal spot F of the radiation source and a center point O of the target section 600 is perpendicular to a surface of a detector 610 at a vertical leg E.

In some embodiments, the fixed location may be represented by position information (e.g., absolute position information and/or relative position information) of the radiation source when the radiation source is located at the fixed location. In some embodiments, the absolute position information may include coordinates of the radiation source in a coordinate system. For example, the absolute position information of the radiation source may include a coordinate (e.g., a longitude, a latitude, and an altitude) of at least one point (e.g., a focal spot) of the radiation source under the world coordinate system. As another example, a three-dimensional (3D) coordinate system may be established based on the X-ray imaging device 110, and the absolute position information may include a coordinate of the at least one point of the radiation source under the 3D coordinate system. In some embodiments, the relative position information may include a positional relationship between the radiation source and a reference object (e.g., the target subject (e.g., the target section of the target subject), the detector, etc.). In some embodiments, the position information of the radiation source may further include a scanning angle of the radiation source.

The detector may be configured to detect the attenuated pre-scan radiation rays emitted from the target subject during the pre-scan, and convert the attenuated pre-scan radiation rays to pre-scan signals. In some embodiments, the detector may include a plurality of detection units arranged in a plurality of rows and/or columns. Each of the plurality of detection units may be made based on semiconductor material(s).

In some embodiments, the processing device 140 may determine the pre-scan imaging data based on the pre-scan signals collected by the detector. In some embodiments, multiple rows of detection units may receive the attenuated pre-scan radiation rays during the pre-scan, and pre-scan signals collected by rows of detection units that correspond to the target section may be obtained for subsequent analysis (e.g., generating the pre-scan imaging data).

In some embodiments, the pre-scan imaging data may be used to determine signal intensities detected by the detection units corresponding to the target section. For example, since the signal intensity detected by a detector unit has a linear correlation with the grey value of a corresponding pixel in the pre-scan imaging data, the processing device 140 may determine a signal intensity detected by the detector unit based on the grey value of the corresponding pixel and the linear correlation.

In some embodiments, the processing device 140 may determine signal intensities detected by a plurality of detector positions at the detector based on the pre-scan imaging data. As used herein, a detector position corresponds to one row of detection units. Merely by way of example, FIG. 6 shows a side view of the detector 610 and the target section 600. Points E and G represent two detection positions of the detector 610. Each of the points E and G corresponds to one row of detection units which is not shown in the side view of the detector 610. In some embodiments, the signal intensity detected by a detector position may be equal to the sum or average of signal intensities detected by the detector units corresponding to the detector position (i.e., the detector units in one row).

In some embodiments, the detection positions may be determined according to experience and/or actual requirements. For example, the detector positions may be determined randomly. As another example, a detector position may be determined for each row of detector units corresponding to the target section. In some embodiments, the distances between any two adjacent detector positions are the same or different. For example, referring to FIG. 9, the distance between any two adjacent detector positions among detector positions $T_1$, $T_2$, $T_3$, $T_4$, . . . , $T_N$ on a detector 910 are the same (e.g., equal to a length PS).

By determining signal intensities detected by the detector positions for subsequent operations, the computation amount of subsequent operations can be reduced, thereby improving the efficiency of exposure parameter determination and/or image reconstruction. In addition, since pre-scan signals generated by detection units not corresponding to the target section are not considered, the subsequent operations can focus on the pre-scan imaging data generated by the one or more detection positions corresponding to the target section, which can reduce noise data from the detection units not corresponding to the target section, thereby improving the accuracy of the exposure parameter determination and/or image reconstruction. In addition, since the target subject is irradiated from one scanning angle during the pre-scan, the radiation damage to the target subject can be reduced.

In some embodiments, the detector may include or be in communication with an output device, for example, a flat panel display (FPD). The output device may be configured to display the pre-scan imaging data (e.g., a 2D image of the target section).

In some embodiments, the processing device 140 may obtain the pre-scan imaging data from the X-ray imaging device (e.g., the X-ray imaging device 110) or a storage device (e.g., the storage device 150, a database, or an external storage) that stores the pre-scan imaging data of the target subject.

In 304, the processing device 140 (e.g., the determination module 220) may determine, based on the pre-scan imaging data, a chord length of at least one chord of the target section.

As used herein, the target section is approximately regarded as an ellipse, and a chord refers to a line connected by two points on a boundary of the ellipse corresponding to the target section.

In some embodiments, an extension line of each of the at least one chord may pass through a focal spot of the radiation source and a detector position of the detector. Merely by way of example, referring to FIG. 6 again, the at least one chord of the target section 600 includes a second chord AB and a first chord CD. An extension line of the second chord AB passes through the focal spot F of the radiation source and a detector position G of the detector 610, and an extension line of the first chord CD passes through the focal spot F of the radiation source and a detector position E of the detector 610.

In some embodiments, the processing device 140 may determine the chord length of each of the at least one chord of the target section through multiple manners, such as, using a machine learning algorithm, a geometric algorithm, etc.

In some embodiments, for each of the at least one chord of the target section, the processing device 140 may determine a first signal intensity detected by the detector position corresponding to the chord based on the pre-scan imaging data, determine a first distance between the focal spot and the detector position corresponding to the chord and a second distance between the focal spot and a ray exit port of the radiation source, and determine the chord length of the chord based on the first signal intensity, the first distance, and the second distance. More descriptions regarding the determination of the chord length of each of the at least one chord may be found in elsewhere in the present disclosure (e.g., FIGS. 4 and 6, and the descriptions thereof).

In 306, the processing device 140 (e.g., the determination module 220) may determine, based on the chord length of the at least one chord of the target section, exposure parameters to be used by the X-ray imaging device in the target scan of the target subject.

For example, the exposure parameters may include a tube voltage, a tube current, a scanning duration, a scanning angle range, a field of view, or the like, or any combination thereof.

In some embodiments, the processing device 140 may determine a shape of the target section based on the chord length of the at least one chord of the target section, and determine the exposure parameters based on the shape of the target section. For example, the target section may be regarded as an ellipse, and the shape of the target section may be determined by determining a major semi-axis and a minor semi-axis of the target section based on the chord length of the at least one chord of the target section. That is, the processing device 140 may determine the exposure parameters based on the major semi-axis and the minor semi-axis of the target section.

In some embodiments, the processing device 140 may determine lengths of a major semi-axis and a minor semi-axis of the target section based on the chord length of the at least one chord of the target section, and determine the exposure parameters based on the lengths of the major semi-axis and the minor semi-axis of the target section. Since the target section is regarded as an ellipse, the major semi-axis is a half of a major axis of the ellipse, and the minor semi-axis is a half of a minor axis of the ellipse.

For illustration purposes, three examples of determining the lengths of the major semi-axis and the minor semi-axis of the target section are provided below.

Example 1

When the at least one chord includes a first chord that passes through a center of the target section and a second chord that does not pass through the center of the target section, the lengths of the major semi-axis and the minor semi-axis of the target section may be determined in the following way. For example, the processing device 140 may determine a first function relating to the lengths of the major semi-axis and the minor semi-axis based on the chord length of the first chord, determine a second function relating to the lengths of the major semi-axis and the minor semi-axis based on the chord length of the second chord, and determine the lengths of the major semi-axis and the minor semi-axis of the target section by solving the first function and the second function. More descriptions regarding the Example 1 may be found in elsewhere in the present disclosure (e.g., FIGS. 5-7, and the descriptions thereof).

Example 2

When the whole target section is within a field of view of the pre-scan, the lengths of the major semi-axis and the minor semi-axis of the target section may be determined in the following way. For example, the processing device 140 may divide the target section into sub-regions based on the at least one chord, determine areas of the sub-regions based on at least part of the chord length of the at least one chord, and determine the lengths of the major semi-axis and the minor semi-axis of the target section based on the areas of the sub-regions. More descriptions regarding the Example 2 may be found in elsewhere in the present disclosure (e.g., FIGS. 8 and 9, and the descriptions thereof).

Example 3

When part of the target section is out of a field of view of the pre-scan, and the at least one chord includes a first chord passing through a center of the target section, the lengths of the major semi-axis and the minor semi-axis of the target section may be determined in the following way. For example, the processing device 140 may determine a first function relating to the lengths of the major semi-axis and the minor semi-axis based on the chord length of the first chord, determine a third function relating to the lengths of the major semi-axis and the minor semi-axis based on a tangent line of the part of the target section, and determine the lengths of the major semi-axis and the minor semi-axis of the target section by solving the first function and the third function. More descriptions regarding the Example 3 may be found in elsewhere in the present disclosure (e.g., FIGS. 10 and 11, and the descriptions thereof).

By considering different conditions of the pre-scan, different manners can be used for determining the lengths of the major semi-axis and the minor semi-axis of the target section, which can improve the accuracy of the length determination, thereby improving the accuracy of subsequent exposure parameter determination and/or the image reconstruction.

In some embodiments, for each of a plurality of scanning angles of the target scan, the processing device 140 may determine, based on the lengths of the major semi-axis and the minor semi-axis of the target section, an equivalent thickness corresponding to the scanning angle. The equivalent thickness corresponding to the scanning angle refers to an estimated traveling distance of radiation rays in the target section when the target section is scanned at the scanning angle. For example, the equivalent thickness corresponding to the scanning angle may be an estimated traveling distance of radiation rays that pass through the center point of the target section when the target section is scanned at the scanning angle. Merely by way of example, an equivalent thickness corresponding to the scanning angle shown in FIG. 6 (indicated by an arrow 650) may be a length of the first chord CD.

In some embodiments, for each of the plurality of scanning angles of the target scan, the processing device 140 may determine exposure parameters corresponding to the scanning angle based on the equivalent thickness corresponding to the scanning angle. For example, if the equivalent thickness corresponding to a scanning angle is relatively large, values of the exposure parameters corresponding to the scanning angle may be relatively large. In some embodiments, exposure parameters for different scanning angles may be determined so that the signal intensities detected by the detector in different scanning angles are close to each other, thereby avoiding an excessive difference in the brightness of image data collected in different scanning angles.

In some embodiments, the exposure parameters may be determined based on the equivalent thickness corresponding to the scanning angles and structural parameters of components of the X-ray imaging device. For example, the structural parameters may include a thickness and/or material of an additional filter (a component of a beam-limiter) of the X-ray imaging device. For instance, additional filters of different thicknesses and/or materials may have different transmittance. Merely by way of example, a transmittance of an additional filter made of copper with a thickness of 0.1 millimeters may be 7.34, a transmittance of an additional filter made of copper with a thickness of 0.1 millimeters and aluminum with a thickness of 1.5 millimeters may be 7.87, a transmittance of an additional filter made of copper with a thickness of 0.2 millimeters may be 8.60, and a transmittance of an additional filter made of copper with a thickness of 0.2 millimeters and aluminum with a thickness of 1.5 millimeters may be 9.07. Further, exposure parameters corresponding to an additional filter that has a relatively little transmittance may be larger than exposure parameters corresponding to an additional filter that has a relatively large transmittance.

In some embodiments, if the target scan corresponds to multiple target sections, the processing device 140 may determine the exposure parameters corresponding to each of the multiple target sections. Alternatively, the processing device 140 may determine a subject model corresponding to the target subject based on the lengths of the major semi-axis and the minor semi-axis of each of the multiple target sections. For each scanning angle and each portion of the target subject, the processing device 140 may determine an equivalent thickness corresponding to the scanning angle and the portion based on the subject model, and determine exposure parameters corresponding to the scanning angle and the portion.

In some embodiments, before determining the exposure parameters, the processing device 140 may verify the lengths of the major semi-axis and the minor semi-axis and determine whether the pre-scan needs to be reperformed. For example, the processing device 140 may obtain reference lengths of the major semi-axis and the minor semi-axis of the target section, and determine whether the pre-scan needs to be reperformed based on the lengths and the reference lengths of the major semi-axis and the minor semi-axis of the target section. If the pre-scan needs to be reperformed, the processing device 140 may obtain second pre-scan imaging data by performing a second pre-scan on the target section, and determine the exposure parameters based on the second pre-scan imaging data. More descriptions regarding the determination of whether the pre-scan needs to be reperformed may be found in elsewhere in the present disclosure (e.g., FIG. 12, and the descriptions thereof).

In 308, the processing device 140 (e.g., the reconstruction module 230) may reconstruct a target image of the target subject based on scan data collected by the X-ray imaging device in the target scan. The target scan may be performed according to the exposure parameters.

The target image refers to an image used for diagnosis and/or treatment. In some embodiments, the processing device 140 may cause the X-ray imaging device (e.g., the X-ray imaging device 110) to perform, based on the exposure parameters, the target scan on the target subject. Further, the processing device 140 may obtain the scan data from the X-ray imaging device 110 or a storage device (e.g., the storage device 150, a database, or an external storage) that stores the scan data of the target subject.

In some embodiments, the processing device 140 may generate the target image by reconstructing the scan data using a reconstruction algorithm. Exemplary reconstruction algorithm may include an iterative reconstruction algorithm, an analytical reconstruction algorithm, a machine learning-based algorithm, or the like, or any combination thereof.

In some embodiments, the processing device 140 may post-process the target image. Exemplary post-processing operations may include image deformation, image enhancement, image denoising, image smoothing, or the like, or any combination thereof.

In some embodiments, the processing device 140 may direct a user terminal to display the target image for a user to view and/or adjust the target image.

According to some embodiments of the present disclosure, the target section can be irradiated by the pre-scan radiation rays emitted by the radiation source located at the fixed location during the pre-scan, and the pre-scan imaging data can be collected for the exposure parameter determination. Since the target subject is irradiated from one scanning angle during the pre-scan, the scanning duration and the radiation damage to the target subject can be reduced.

It should be noted that the descriptions of the process 300 are provided for illustration purposes, and not intended to limit the scope of the present disclosure. For example, if the target scan is a spiral scan directed to a region of interest of the target subject, pre-scan imaging data relating to a plurality of target sections of the region of interest may be obtained, and exposure parameters for each target section may be determined by performing operations 300 for the target section.

FIG. 4 is a flowchart illustrating an exemplary process 400 for determining a chord length of a chord of a target section according to some embodiments of the present disclosure. In some embodiments, the process 400 may be performed to achieve at least part of operation 304 as described in connection with FIG. 3. For example, the process 400 may be determined for each of the at least one chord of the target section.

In 402, the processing device 140 (e.g., the determination module 220) may determine, based on pre-scan imaging data, a first signal intensity detected by a detector position corresponding to a chord.

As described above, an extension line of each chord passes through a detector position of the detector, and each detector position corresponds to one row of detection units of the detector. The detector position corresponding to a chord refers to a detector position passed by the extension line of the chord. The first signal intensity of the detector position is the sum or average of the row of detection units corresponding to the detector position. Merely by way of example, for the first chord CD in FIG. 6, a first signal intensity detected by the detector position E is determined; for the second chord AB in FIG. 6, a first signal intensity detected by the detector position G is determined. More descriptions regarding the determination of a signal intensity detected by a detector position may be found elsewhere in the present disclosure. See, e.g., operation 302 and relevant descriptions thereof.

In 404, the processing device 140 (e.g., the determination module 220) may determine a first distance between a focal spot of the radiation source and the detector position corresponding to the chord and a second distance between the focal spot and a ray exit port of the radiation source.

Merely by way of example, referring to FIG. 6, for the first chord CD, a first distance $S_1$ is a distance from the focal spot F to the detector position E, and a second distance $S_2$ is a distance from the focal spot F to a ray exit port Q.

In some embodiments, the first distance may be determined based on the position of the focal spot, the position of the detector, and the position of the target section with respect to the target subject. In some embodiments, the processing device 140 may obtain an optical image of the X-ray imaging device (e.g., an optical image including the radiation source, the detector, and the target subject), and determine the first distance based on the optical image. In some embodiments, the second distance may be a preset distance relating to the geometric structure of the radiation source.

In 406, the processing device 140 (e.g., the determination module 220) may determine a chord length of the chord based on the first signal intensity, the first distance, and the second distance.

In some embodiments, the processing device 140 may determine a second signal intensity at the ray exit port of the radiation source. The second signal intensity refers to a signal intensity of the pre-scan radiation rays that are emitted from the ray exit port and have not passed through the target section of the target subject and the atmosphere. For example, a signal intensity detector may be disposed on the ray exit port, and the processing device 140 may obtain a detected signal intensity from the signal intensity detector and determine the detected signal intensity as the second signal intensity. As another example, the processing device 140 may determine the second signal intensity based on the exposure parameters used in the pre-scan, a thickness and/or material of the additional filter, and a correction coefficient.

Further, the processing device 140 may determine the chord length of the chord based on the first signal intensity, the second signal intensity, the first distance, and the second distance. For example, the processing device 140 may determine a fourth function relating to in-vitro attenuation based on the second signal intensity, the first distance, and the second distance, and a fifth function relating to in-vivo attenuation based on the first signal intensity. The in-vitro attenuation refers to the attenuation of the pre-scan radiation rays when passing through the atmosphere outside the target subject. The in-vivo attenuation refers to the attenuation of the pre-scan radiation rays when passing through the target subject. Further, the processing device 140 may determine the chord length of the chord by solving the fourth function and the fifth function.

Merely by way of example, the fourth function may be represented as Equation (1):

$$I_0 = Q \times (S_2 / (S_1 - L))^2, \quad (1)$$

where $I_0$ refers to an in-vitro attenuation signal intensity; Q refers to the second signal intensity; $S_2$ refers to the second distance between the focal spot and the ray exit port of the radiation source; $S_1$ refers to the first distance between the focal spot of the radiation source and the detector position corresponding to the chord; L refers to the chord length of the chord; and $S_1 - L$ refers to a distance that the pre-scan radiation rays pass through in the atmosphere outside the target section.

For example, referring to FIG. 6, a distance between the focal spot F of the radiation source and the detector position E corresponding to the first chord CD is the first distance $S_1$, and a distance between the focal spot F of the radiation source and the ray exit port Q of the radiation source is the second distance $S_2$. A distance that the pre-scan radiation rays pass through in the atmosphere outside the target section is $S_1 - L$, which is equal to the sum of the distance n and the distance m denoted in FIG. 6. The distance n refers to the distance that the pre-scan radiation rays travel from the focal spot F of the radiation source to a surface point D of the target section 600. The distance m refers to the distance that the pre-scan radiation rays travel from a surface point C of the target section 600 to the detector position E corresponding to the first chord CD.

The fifth function may be represented as Equation (2):

$$I = I_0 \times e^{(-uL)}, \quad (2)$$

where l refers to the first signal intensity; and u refers to an average attenuation coefficient.

In some embodiments, the average attenuation coefficient u may be determined based on the tube voltage of the pre-scan, the thickness of the filter of the X-ray imaging device, and the material of the target subject. For example, the processing device 140 may determine the average attenuation coefficient u by retrieving a reference table of average attenuation coefficients of different tube voltages, different thicknesses of the filter, and different materials.

Unknowns in the fourth function and the fifth function may include the in-vitro attenuation signal intensity $I_0$ and the chord length of the chord L. Therefore, the processing device 140 may determine the chord length of the chord by solving the fourth function and the fifth function. For example, referring to FIG. 6 again, a chord length of the first chord CD may be determined by substituting a first signal intensity detected by the detector position E into the fifth function, and a chord length of the second chord AB may be determined by substituting a first signal intensity detected by the detector position G into the fifth function.

FIG. 5 is a flowchart illustrating an exemplary process 500 for determining lengths of a major semi-axis and a minor semi-axis of a target section according to some embodiments of the present disclosure. In some embodiments, the process 500 may be performed to achieve at least part of operation 306 as described in connection with FIG. 3.

Figure 7:
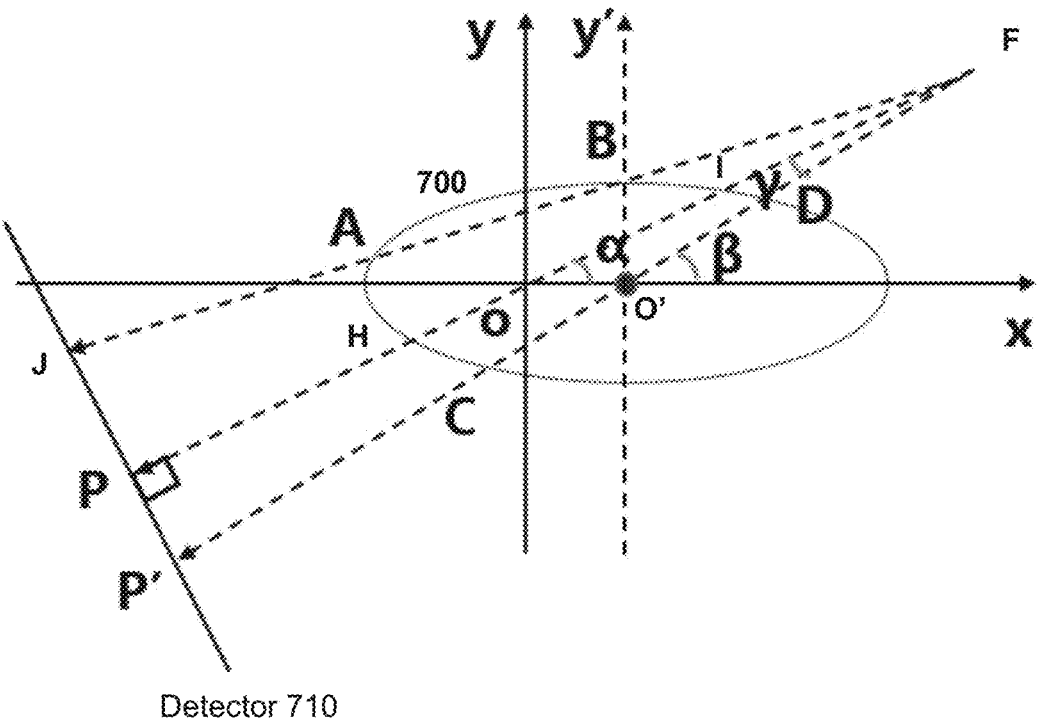
FIG. 7 is a schematic diagram illustrating an exemplary target section of Example 1 according to some embodiments of the present disclosure.

In some embodiments, at least one chord may include a first chord and a second chord, the first chord may pass through a center of a target section, and the second chord may not pass through the center of the target section. For example, as shown in FIG. 6, at least one chord of the target section 600 includes the first chord CD and the second chord AB, the first chord CD passes through the center O of the target section 600 and is perpendicular to the detector 610, and the second chord AB does not pass through the center O of the target section 600. As another example, as shown in FIG. 7, at least one chord of a target section 700 includes a first chord CD and a second chord AB, the first chord CD passes through a center O' of a target section 700 and is not perpendicular to a detector 710, and the second chord AB does not pass through the center O' of the target section 700. Lengths of a major semi-axis and a minor semi-axis of the target section may be determined in the following way.

In 502, the processing device 140 (e.g., the determination module 220) may determine a first function relating to lengths of a major semi-axis and a minor semi-axis based on a chord length of a first chord.

The first chord refers to a chord that passes through a center of the target section of the target subject. For example, since signal attenuation of pre-scan radiation rays passing through the center of the target section is maximum, a detector position of the detector corresponding to a minimum signal intensity or a minimum grayscale value may be determined as an intersection point of an extension line of the first chord and the detector.

In some embodiments, the processing device 140 may determine whether the first chord is perpendicular to a detector. For example, the processing device 140 may determine whether the first chord is perpendicular to the detector by determining whether the first chord passes through an isocenter of a C-arm of an X-ray imaging device. If the first chord passes through the isocenter of the C-arm of the X-ray imaging device, the processing device 140 may determine that the first chord is perpendicular to the detector. As another example, the processing device 140 may determine whether the first chord is perpendicular to the detector by determining whether a center of a target section coincides with the isocenter of the C-arm of the X-ray imaging device. If the center of the target section coincides with the isocenter of the C-arm of the X-ray imaging device, the processing device 140 may determine that the first chord is perpendicular to the detector.

When the first chord is perpendicular to the detector, the processing device 140 may determine the first function based on the chord length of the first chord and an orientation of the first chord. The orientation of the first chord may be represented by an included angle between the first chord and a horizontal direction (e.g., an x axis) or a vertical direction (e.g., a y axis). For example, referring to FIG. 6, the first chord CD may be perpendicular to the detector 610 at the detector position E, and the first function may be determined based on the chord length of the first chord CD. For example, the first function may be represented as Equation (3) below:

$$L_{CD} = \frac{2 \times b}{\sqrt{1 - \left(1 - \frac{b^2}{a^2}\right) \times (\sin\theta)^2}}, \tag{3}$$

where $L_{CD}$ refers to the chord length of the first chord CD; b refers to the length of the minor semi-axis; $\alpha$ refers to the length of the major semi-axis; and $\theta$ refers to an included angle between the first chord and the y axis.

When the first chord is not perpendicular to the detector, the processing device 140 may determine a reference chord that is perpendicular to the detector, determine a reference distance between the detector position corresponding to the first chord and a detector position corresponding to the reference chord, and determine the first function based on the chord length of the first chord, the reference distance, and an orientation of the reference chord.

Merely by way of example, referring to FIG. 7, the first chord CD is not perpendicular to the detector 710. An extension line of the first chord CD intersects with the detector 710 at a detector position P', and the detector position P' may correspond to a minimum signal intensity or a minimum grayscale value. The center O' of the target section 700 does not coincide with an isocenter O of a C-arm of an X-ray imaging device. In other words, there is a distance between the center O' and the isocenter O. A reference chord HI that is perpendicular to the detector 710 may be determined by determining a minimum distance between a focal spot F of a radiation source and the detector 710. A chord length of the reference chord HI may be determined in a similar manner as how the chord length of the first chord is determined as illustrated in FIG. 4. A reference distance PP' between the detector position P' corresponding to the first chord and the detector position P corresponding to the reference chord may be determined. For example, the reference distance PP' may be determined based on a structure of the detector 710, the position of the detector position P', and the position of the detector position P. The first function may be determined based on the chord length of the first chord CD, the reference distance PP', and an orientation of the reference chord HI. For example, the first function may be shown as Equation (4) below:

$$L_{CD} = \frac{2 \times b}{\sqrt{1 - \left(1 - \frac{b^2}{a^2}\right) \times \left(\sin\left(\frac{\pi}{2} - \beta\right)\right)^2}}, \tag{4}$$

where $\beta$ refers to an included angle between the first chord and the x axis.

$\beta$ is equal to a sum of an included angle $\gamma$ between the first chord CD and the reference chord HI and an included angle $\alpha$ between the reference chord HI and the y axis. The included angle $\gamma$ may be determined based on the reference distance PP' and a distance from the focal spot F to the detector position P of the detector (i.e., the minimum distance between the focal spot F of the radiation source and the detector 710).

In 504, the processing device 140 (e.g., the determination module 220) may determine a second function relating to the lengths of the major semi-axis and the minor semi-axis based on a chord length of a second chord.

The second chord refers to a chord that does not pass through the center of the target section of the target subject. The second chord may be any chord of the target section other than the first chord. For example, referring to FIG. 6, the processing device 140 may determine a midpoint between the detector position E and an edge point of the detector 610, and designate the midpoint as the detector position G. The second chord AB may be determined based on the target section 600 and a connection line of the focal spot F and the detector position G.

When the first chord is perpendicular to the detector, the processing device 140 may determine a slope of the second chord based on a third distance between the detector position corresponding to the first chord and the detector position corresponding to the second chord, a fourth distance between the focal spot and the detector position corresponding to the first chord, and the orientation of the first chord. The processing device 140 may determine a coordinate of the focal spot in a coordinate system whose origin is located at the center of the target section, and determine a linear equation representing the second chord based on the slope of the second chord and the coordinate of the focal spot. The processing device 140 may determine the second function relating to the lengths of the major semi-axis and the minor semi-axis based on the chord length of the second chord and the linear equation.

Merely by way of example, referring to FIG. 6 again, a coordinate system xoy corresponding to the target section 600 may be established, and an origin of the coordinate system may be located at the center O of the target section 600 (i.e., an isocenter of an X-ray imaging device). A third distance $P_1$ between the detector position E (an intersection point of the extension line of the first chord CD and the detector 610) and the detector position G (an intersection point of the extension line of the second chord AB and the detector 610) may be determined. A fourth distance $S_1$ between the focal spot and the detector position corresponding to the first chord may be determined in a similar manner as how the first distance is determined as described in FIG. 4.

Since the triangle EFG is a right triangle, an included angle between the first chord CD and the second chord AB may be $\arctan(P_1/S_1)$. An included angle between the second chord AB and the x axis may be $\pi/2 - \theta - \arctan(P_1/S_1)$. Therefore, a slope of the second chord AB may be determined based on the included angle between the second chord AB and the x axis. That is, the slope of the second chord AB may be $\tan(\pi/2 - \theta - \arctan(P_1/S_1))$. A coordinate of the focal spot F in the coordinate system corresponding to the target section 600 may be $(P_2 \times \cos(\pi/2 - \theta), P_2 \times \sin(\pi/2 - \theta))$. The $P_2$ refers to a distance from the focal spot F to the center O. In some embodiments, when the radiation source is positioned at the fixed location, the distance $P_2$ may be determined, for example, using a laser range finder, etc.

A linear equation representing the second chord AB may be determined based on the slope of the second chord AB and the coordinate of the focal spot F. For example, the linear equation may be represented as Equation (5) below:

$$y = kx + c, \tag{5}$$

where k refers to the slope of the second chord AB (i.e., $k=\tan(\pi/2-\theta-\arctan(P1/S1)))$; c refers to an intercept of the second chord AB; x refers to an abscissa of a point on the second chord AB; and y refers to an ordinate of the point on the second chord AB.

The intercept c of the second chord AB may be determined by substituting the coordinate $(P_2 \times \cos(\pi/2-\theta), P_2 \times \sin(\pi/2-\theta))$ of the focal spot F into the Equation (5), and the linear equation representing the second chord AB may be determined.

An ellipse function of the target section 600 may be represented as Equation (6):

$$\left(\frac{x}{a}\right)^2 + \left(\frac{y}{b}\right)^2 = 1. \tag{6}$$

Since the second chord AB and the target section 600 intersect at the points A and B, coordinates of the points A and B may be determined by solving the Equation (5) and Equation (6). For example, assuming that a and b are known, the coordinates of the points A and B may be represented as $(x_1=f_x(a, b), \; y_1=f_y(a, b))$ and $(x_2=g_x(a, b), \; y_2=g_y(a, b))$, respectively.

The second function relating to the lengths of the major semi-axis and the minor semi-axis may be determined based on the chord length of the second chord. For example, the second function may be shown as Equation (7):

$$L_{AB} = \sqrt{(x_1 - x_2)^2 + (y_1 - y_2)^2}, \tag{7}$$

where $x_1$ refers to an abscissa of the point A; $y_1$ refers to an ordinate of the point A; $x_2$ refers to an abscissa of the point B; $y_2$ refers to an ordinate of the point B.

The second function may be determined by substituting the coordinates $(x_1=f_x(a, b), \; y_1=f_y(a, b))$ and $(x_2=g_x(a, b), \; y_2=g_y(a, b))$ into the Equation (7). Therefore, the Equation (7) may be converted to an equation whose unknowns are a and b (also referred to a converted Equation (7)).

When the first chord is not perpendicular to the detector, the second function may be determined in a similar manner as how the converted Equation (7)) is determined, except the linear equation representing the second chord AB is determined in a different manner as described below.

Merely by way of example, referring to FIG. 7 again, a coordinate system xoy corresponding to an X-ray imaging device may be established, and an origin of the coordinate system xoy may be located at an isocenter of the C-arm of the X-ray imaging device. A coordinate system xo'y' corresponding to the target section 700 may be established, and an origin of the coordinate system xo'y' may be located at the center O' of the target section 700. A distance OO' may exist between the center O' of the target section 700 and an isocenter of an X-ray imaging device. Therefore, a transformation relationship between the coordinate system xoy and coordinate system xo'y' may be that for each point in the coordinate system xoy, an abscissa of the point in the coordinate system xoy may be equal to a sum of an abscissa of a corresponding point in the coordinate system xo'y' and the distance OO', and an ordinate of the point in the coordinate system xoy may be the same as an ordinate of a corresponding point in the coordinate system xo'y'.

When the radiation source is positioned at the fixed location, a distance OF may be determined, for example, using a laser range finder, etc. Therefore, a coordinate of a focal spot F of the radiation source in the coordinate system xoy may be (OF×cos α, OF×sin α). A distance O'F may be equal to OF×sin α/sin β, and a coordinate of the focal spot F of the radiation source in the coordinate system xo'y' may be (OF×sin α/tan β, OF×sin α). Correspondingly, the distance OO' may be equal to OF×cos α−OF×sin α/tan β.

A fifth distance JP between the detector position P (an intersection point of the extension line of the reference chord HI and the detector 710) and a point J (an intersection point of the extension line of the second chord AB and the detector 710) may be determined. A sixth distance PF between the focal spot F and the detector position corresponding to the reference chord HI may be determined in a similar manner as how the first distance is determined as described in FIG. 4.

Since a triangle JFP is a right triangle, an included angle between the reference chord HI and the second chord AB may be arctan(PF/JP). An included angle between the second chord AB and the x axis may be α−arctan(PF/JP). Therefore, a slope of the second chord AB may be determined based on the included angle between the second chord AB and the x axis. That is, the slope of the second chord AB may be tan(α−arctan(PF/JP)).

A linear equation representing the second chord AB may be determined based on the slope of the second chord AB and the coordinate of the focal spot F in the coordinate system xo'y'. For example, the linear equation may be represented as Equation (8):

$$y = kx + c. \tag{8}$$

At this time, the slope k of the second chord AB may be equal to tan(α−arctan(PF/JP)).

The intercept c of the second chord AB may be determined by substituting the coordinate (OF×sin α/tan β, OF×sin α) of the focal spot F into the Equation (8), and the linear equation representing the second chord AB may be determined.

In 506, the processing device 140 (e.g., the determination module 220) may determine the lengths of the major semi-axis and the minor semi-axis of the target section by solving the first function and the second function.

For example, a function set may be determined by combining the first function and the second function, and the lengths of the major semi-axis and the minor semi-axis of the target section by solving the function set.

According to some embodiments of the present disclosure, whether the first chord is perpendicular to the detector is determined, and different approaches are adopted to determine the first function and the second function based on a determination result of whether the first chord is perpendicular to the detector. In this way, the positioning error of the target subject during the pre-scan can be considered, which can improve the accuracy of the first function and second function, and the accuracy of subsequent operations (e.g., the exposure parameter determination and/or the image reconstruction).

Figure 8:
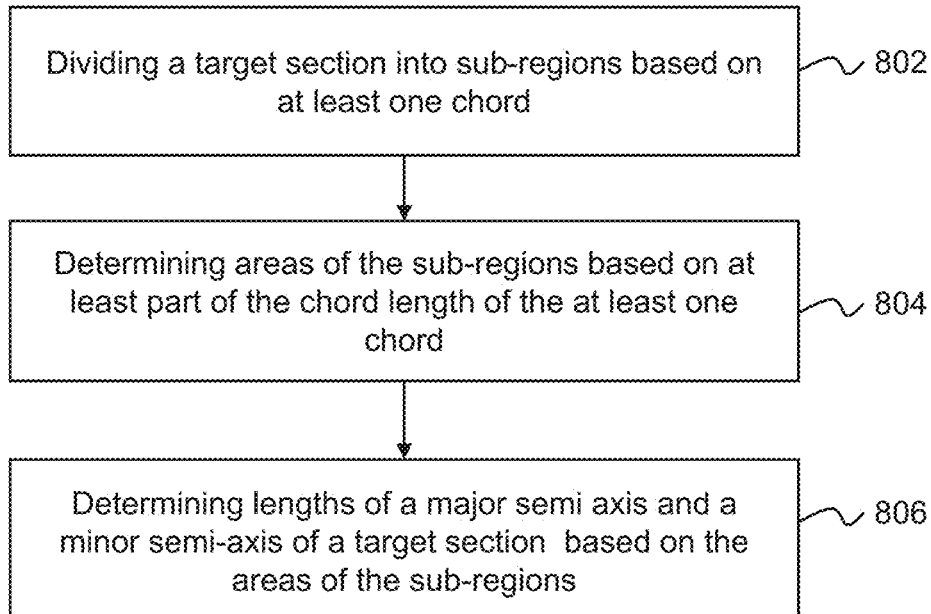
FIG. 8 is a flowchart illustrating an exemplary process for determining lengths of a major semi-axis and a minor semi-axis of a target section according to some embodiments of the present disclosure.

FIG. 8 is a flowchart illustrating an exemplary process 800 for determining lengths of a major semi-axis and a minor semi-axis of a target section according to some embodiments of the present disclosure. In some embodiments, the process 800 may be performed to achieve at least part of operation 306 as described in connection with FIG. 3.

Figure 9:
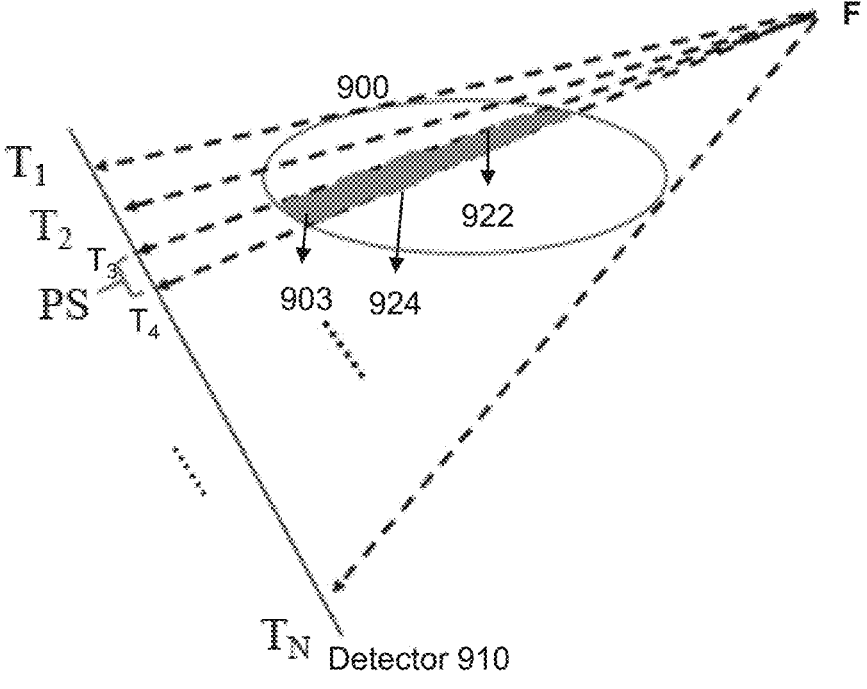
FIG. 9 is a schematic diagram illustrating an exemplary target section of Example 2 according to some embodiments of the present disclosure.

In some embodiments, as shown in FIG. 9, the whole target section 900 is within a field of view of a pre-scan. Lengths of a major semi-axis and a minor semi-axis of the target section 900 may be determined in the following way.

In 802, the processing device 140 (e.g., the determination module 220) may divide a target section into sub-regions based on at least one chord.

For example, as shown in FIG. 9, a plurality of chords (e.g., chords corresponding to connection lines $FT_1$, $FT_2$, $FT_3$, $FT_4$, ..., $FT_N$) may divide the target section 900 into sub-regions. Each sub-region may be defined by one or more chords and a boundary of the target section 900. For instance, a sub-region 903 is defined by a chord 922, a chord 924, and the boundary of the target section 900.

In some embodiments, each sub-region may be approximately regarded as a triangle or a trapezoid.

In 804, the processing device 140 (e.g., the determination module 220) may determine areas of the sub-regions based on at least part of the chord length of the at least one chord.

For example, referring to FIG. 9 again, if the sub-region 903 is regarded as a triangle, an area of the sub-region 903 may be determined based on the chord 922 (or the chord 924) and a distance PS. For instance, the area of the sub-region 903 may be determined according to Equation (9) below:

$$S = \frac{l \times PS}{2},\qquad(9)$$

where S refers to the area of the sub-region 903; l refers to a chord length of the chord 922 (or the chord 924); and PS refers to the distance PS.

As another example, if the sub-region 903 is regarded as a trapezoid, an area of the sub-region 903 may be determined based on the chord 922, the chord 924, and the distance PS. For instance, the area of the sub-region 903 may be determined according to Equation (10) below:

$$S = \frac{(l_1 + l_2) \times PS}{2},\qquad(10)$$

where $l_1$ refers to a chord length of the chord 922; and $l_2$ refers to a chord length of the chord 924.

In 806, the processing device 140 (e.g., the determination module 220) may determine lengths of a major semi-axis and a minor semi-axis of the target section based on the areas of the sub-regions.

In some embodiments, the processing device 140 may determine an area of the target section by determining a summation of the areas of the sub-regions, and determine an area function of the target section. The area function of the target section may be shown as Equation (11):

$$S = \pi \times a \times b,\qquad(11)$$

where S refers to the area of the target section; and 7 refers to a circular constant.

The processing device 140 may determine a first function relating to lengths of a major semi-axis and a minor semi-axis based on a chord length of a first chord. More descriptions regarding the determination of the first function may be found in elsewhere in the present disclosure (e.g., FIG. 5 and the descriptions thereof). The processing device 140 may further determine the lengths of the major semi-axis and the minor semi-axis of the target section based on the area function and the first function. For example, a function set may be determined by combining the first function and the area function, and the lengths of the major semi-axis and the minor semi-axis of the target section by solving the function set.

Figure 10:
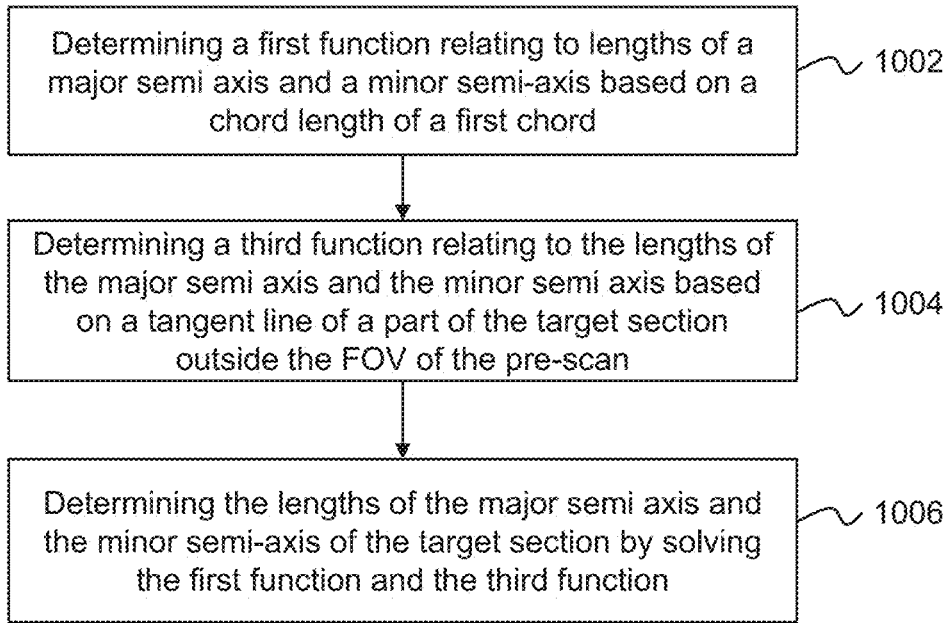
FIG. 10 is a flowchart illustrating an exemplary process for determining lengths of a major semi-axis and a minor semi-axis of a target section according to some embodiments of the present disclosure.

FIG. 10 is a flowchart illustrating an exemplary process 1000 for determining lengths of a major semi-axis and a minor semi-axis of a target section according to some embodiments of the present disclosure. In some embodiments, the process 1000 may be performed to achieve at least part of operation 306 as described in connection with FIG. 3.

Figure 11:
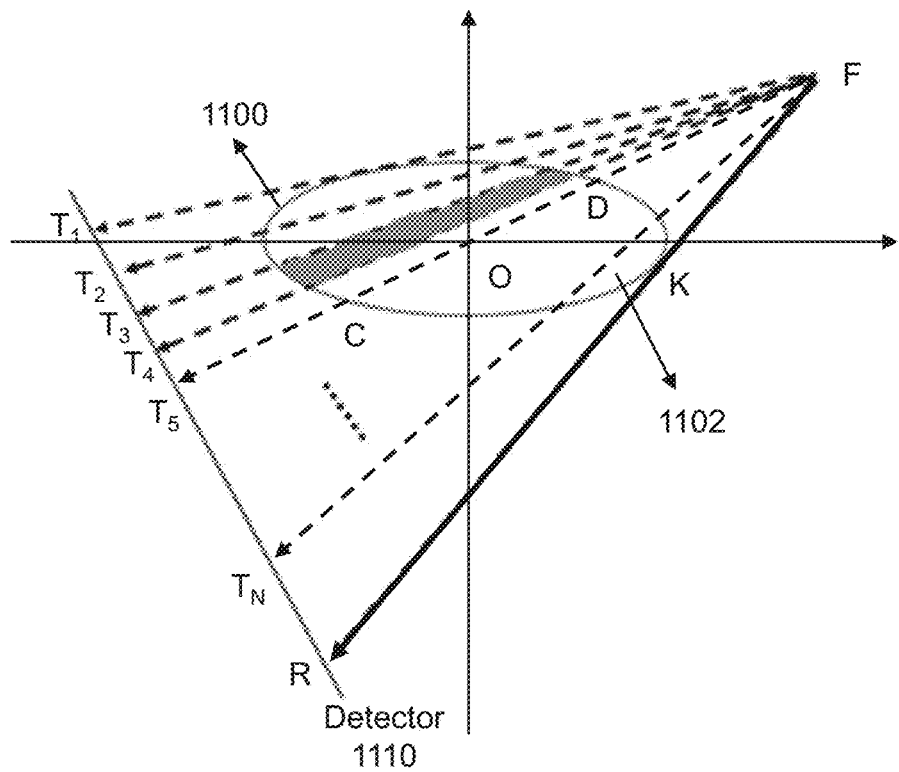
FIG. 11 is a schematic diagram illustrating an exemplary target section of Example 3 according to some embodiments of the present disclosure.

In some embodiments, as shown in FIG. 11, dotted lines represent pre-scan radiation rays emitted in the pre-scan, part (e.g., a region 1102) of a target section 1100 is out of a field of view (e.g., a region $T_1FT_N$) of the pre-scan, and at least one chord may include a first chord CD passing through a center O of the target section 1100. Lengths of a major semi-axis and a minor semi-axis of the target section may be determined in the following way.

In 1002, the processing device 140 (e.g., the determination module 220) may determine a first function relating to lengths of a major semi-axis and a minor semi-axis based on a chord length of a first chord.

Operation 1002 may be performed in a similar manner as operation 502, and the descriptions thereof are not repeated here.

In 1004, the processing device 140 (e.g., the determination module 220) may determine a third function relating to the lengths of the major semi-axis and the minor semi-axis based on a tangent line of a part of the target section outside the FOV of the pre-scan.

In some embodiments, since the part of the target section is out of a field of view of a pre-scan, pre-scan imaging data does not include imaging data relating to the part of the target section. The processing device 140 may determine image data of the target section by processing the pre-scan imaging data using an extrapolation algorithm. For example, image data of the target section 1100 may be determined by determining an edge of the region 1102 based on the pre-scan imaging data.

In some embodiments, the processing device 140 may determine the tangent line of the part of the target section based on the image data of the target section. For example, as shown in FIG. 11, a tangent line RF may be tangent to the target section 1100 at a point K.

A linear equation representing the tangent line RF may be determined in a similar manner as how the linear equation representing the second chord AB is determined as described in operation 504. For example, the linear equation representing the tangent line RF may be similar to Equation (8) representing the second chord AB.

Since the tangent line and the target section only intersect at one point, an equation set of the linear equation representing the tangent line and an ellipse function of the target section only include one solution. Therefore, the equation set may be converted to an equation including one unknown. For example, the equation including one unknown may be represented as Equation (12):

$$\left(\frac{x}{a}\right)^2 + \left(\frac{kx+c}{b}\right)^2 = 1. \tag{12}$$

Since the Equation (12) only includes one solution, a value of a discriminant corresponding to the Equation (12) is equal to 0, and the third function may be determined according to the value (0) of the discriminant. That is, the third function may be represented as Equation (13):

$$\left(\frac{2kc}{b}\right)^2 = 4 \times \left(\frac{1}{a^2} + \left(\frac{k}{b}\right)^2\right) \times \left(\frac{c^2 - b^2}{b^2}\right). \tag{13}$$

At this time, the Equation (13) includes unknowns a and b.

In 1006, the processing device 140 (e.g., the determination module 220) may determine the lengths of the major semi-axis and the minor semi-axis of the target section by solving the first function and the third function.

For example, a function set may be determined by combining the first function and the third function, and the lengths of the major semi-axis and the minor semi-axis of the target section by solving the function set.

Figure 12:
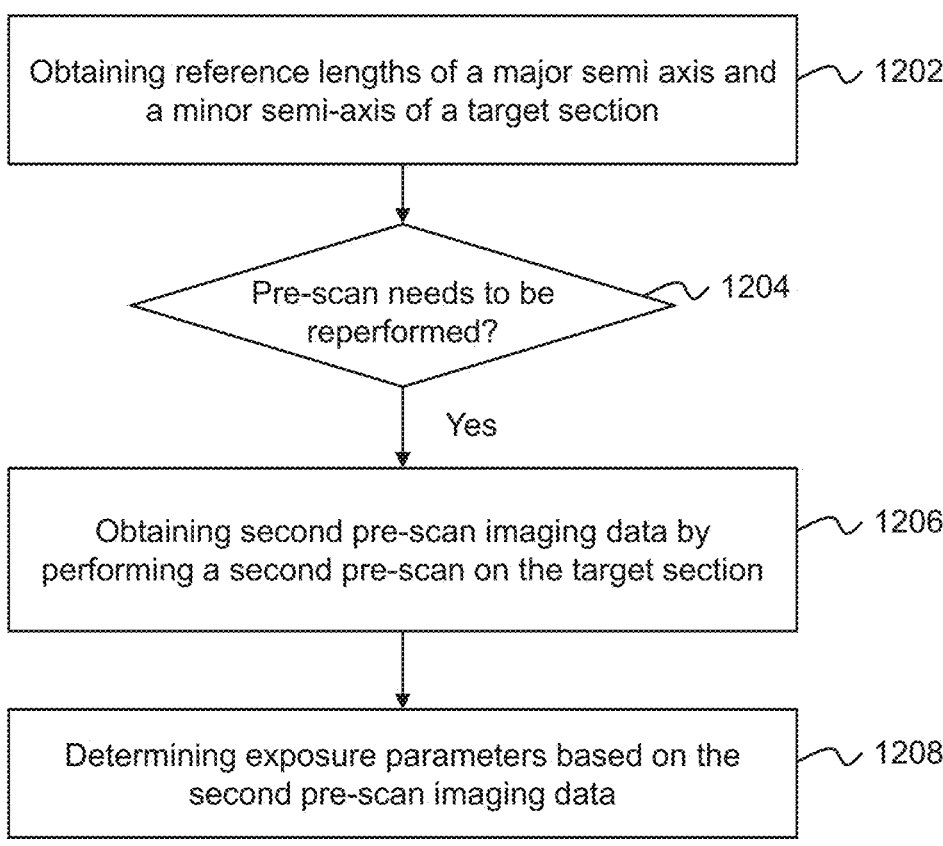
FIG. 12 is a flowchart illustrating an exemplary process for determining whether a pre-scan needs to be reperformed according to some embodiments of the present disclosure.

FIG. 12 is a flowchart illustrating an exemplary process 1200 for determining whether a pre-scan needs to be reperformed according to some embodiments of the present disclosure. In some embodiments, the process 1200 may be performed to achieve at least part of operation 306 as described in connection with FIG. 3.

In 1202, the processing device 140 (e.g., the determination module 220) may obtain reference lengths of a major semi-axis and a minor semi-axis of a target section.

The reference lengths may be used to determine whether lengths of the major semi-axis and the minor semi-axis of the target section determined based on pre-scan imaging data are reasonable. For example, the reference lengths may be length ranges of the major semi-axis and the minor semi-axis of the target section. As another example, the reference lengths may be statistical values of the lengths of the major semi-axis and the minor semi-axis of a human section. Specifically, the human section may correspond to the same body part as the target subject.

In some embodiments, the processing device 140 may determine the reference lengths according to historical data. The historical data may include lengths of a major semi-axis and a minor semi-axis of each of a plurality of sections determined in historical scans. For example, the processing device 140 may obtain historical data of sections similar to the target section (e.g., sections belonging to the same body part, similar subjects), and determine the reference lengths based on the historical data.

In some embodiments, the processing device 140 may determine the reference lengths according to optical imaging data. For example, the processing device 140 may obtain the optical imaging data of the target subject, and generate a human body model of the target subject based on the optical imaging data. The processing device 140 may determine the reference lengths based on the human body model.

In 1204, the processing device 140 (e.g., the determination module 220) may determine whether the pre-scan needs to be reperformed based on the lengths and the reference lengths of the major semi-axis and the minor semi-axis of the target section.

For example, if the reference lengths are length ranges of the major semi-axis and the minor semi-axis, the processing device 140 may determine whether the lengths of the major semi-axis and the minor semi-axis of the target section are within their corresponding length ranges, respectively. If the lengths of the major semi-axis and the minor semi-axis of the target section are within their corresponding length ranges, respectively, the processing device 140 may determine that the pre-scan does not need to be reperformed. Otherwise, the processing device 140 may determine that the pre-scan needs to be reperformed.

As another example, if the reference lengths are statistical values of lengths of the major semi-axis and the minor semi-axis, the processing device 140 may determine whether the difference between the lengths and the reference lengths is less than or equal to a difference threshold. If the length difference is less than or equal to the difference threshold, the processing device 140 may determine that the pre-scan does not need to be reperformed. Otherwise, the processing device 140 may determine that the pre-scan needs to be reperformed.

If the pre-scan does not need to be reperformed, the processing device 140 may determine exposure parameters based on the pre-scan imaging data. More descriptions regarding the determination of the exposure parameters may be found in elsewhere in the present disclosure (e.g., FIG. 3 and the descriptions thereof).

If the pre-scan needs to be reperformed, the processing device 140 may proceed to operation 1206.

In 1206, the processing device 140 (e.g., the determination module 220) may obtain second pre-scan imaging data by performing a second pre-scan on the target section.

The second pre-scan imaging data may be obtained in a similar manner as how the pre-scan imaging data is obtained as described in operation 302. For example, the processing device 140 may obtain second pre-scan parameters by updating pre-scan parameters of the last pre-scan, and direct the X-ray imaging device to perform the second pre-scan on the target section based on the second pre-scan parameters to obtain the second pre-scan imaging data.

In 1208, the processing device 140 (e.g., the determination module 220) may determine the exposure parameters based on the second pre-scan imaging data.

The exposure parameters may be determined based on the second pre-scan imaging data in a similar manner as how the exposure parameters are determined as described in operation 306, which is not repeated herein.

According to some embodiments of the present disclosure, the lengths of the major semi-axis and the minor semi-axis of the target section are verified before determining the exposure parameters, which can improve the accuracy of the exposure parameter determination and/or image reconstruction.

Figure 13:
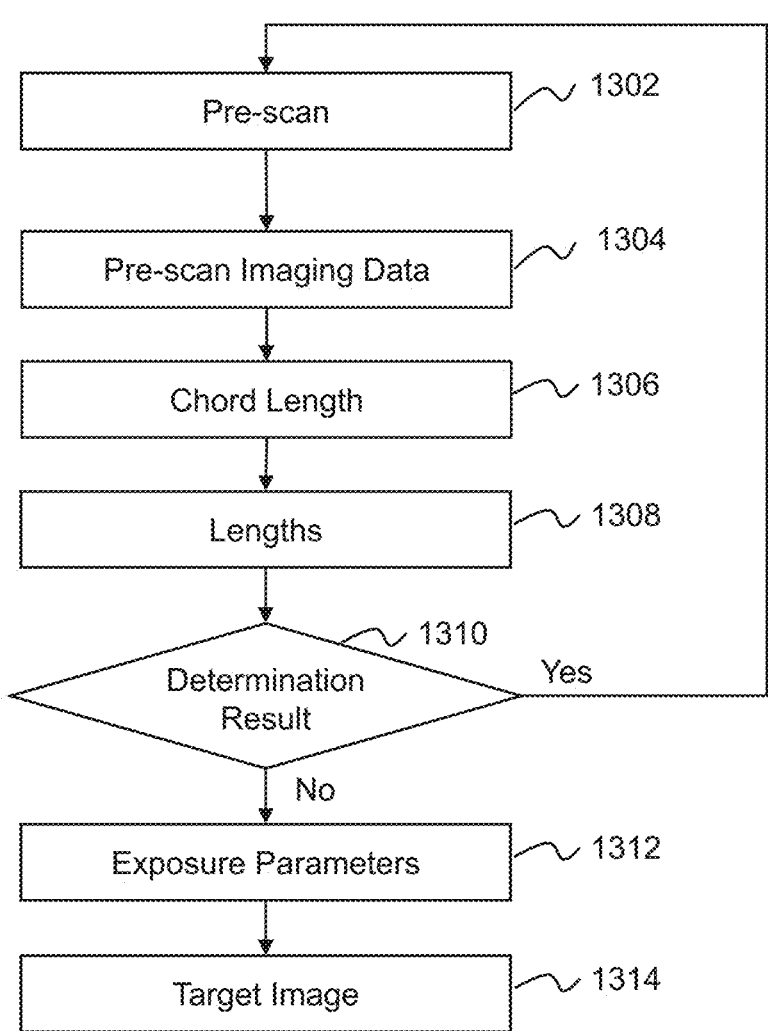
FIG. 13 is a flowchart illustrating an exemplary process for image reconstruction according to some embodiments of the present disclosure.

FIG. 13 is a schematic diagram illustrating an exemplary process 1300 for image reconstruction according to some embodiments of the present disclosure.

A pre-scan 1302 may be performed on a target section of a target subject, and pre-scan imaging data 1304 relating to the target section of the target subject may be obtained. A chord length 1306 of at least one chord of the target section may be determined based on the pre-scan imaging data 1304. Lengths 1308 of a major semi-axis and a minor semi-axis of the target section may be determined based on the chord length 1306 of the at least one chord of the target section. A determination result 1310 of whether the pre-scan 1302 needs to be reperformed may be determined based on the lengths 1308 of the major semi-axis and the minor semi-axis of the target section. If the pre-scan does not need to be reperformed, exposure parameters 1312 to be used in a target scan of the target subject may be determined based on the lengths 1308 of the major semi-axis and the minor semi-axis of the target section.

If the pre-scan needs to be reperformed, a second pre-scan (e.g., a new pre-scan 1302) may be performed on the target section, and a second pre-scan imaging data (e.g., new pre-scan imaging data 1304) may be obtained. Correspondingly, the exposure parameters 1312 may be determined based on the second pre-scan imaging data.

The target scan may be performed according to the exposure parameters 1312, and a target image 1314 of the target subject may be reconstructed based on scan data collected in the target scan.

It should be noted that the descriptions of the processes 300-500, 800, 1000, and 1200 are provided for the purposes of illustration, and are not intended to limit the scope of the present disclosure. For persons having ordinary skills in the art, various variations and modifications may be conducted under the teaching of the present disclosure. For example, the processes 300-500, 800, 1000, and 1200 may be accomplished with one or more additional operations not described, and/or without one or more of the operations discussed. Additionally, the order in which the operations of the processes 300-500, 800, 1000, and 1200 are not intended to be limiting. However, those variations and modifications may not depart from the protection of the present disclosure.

Figure 14:
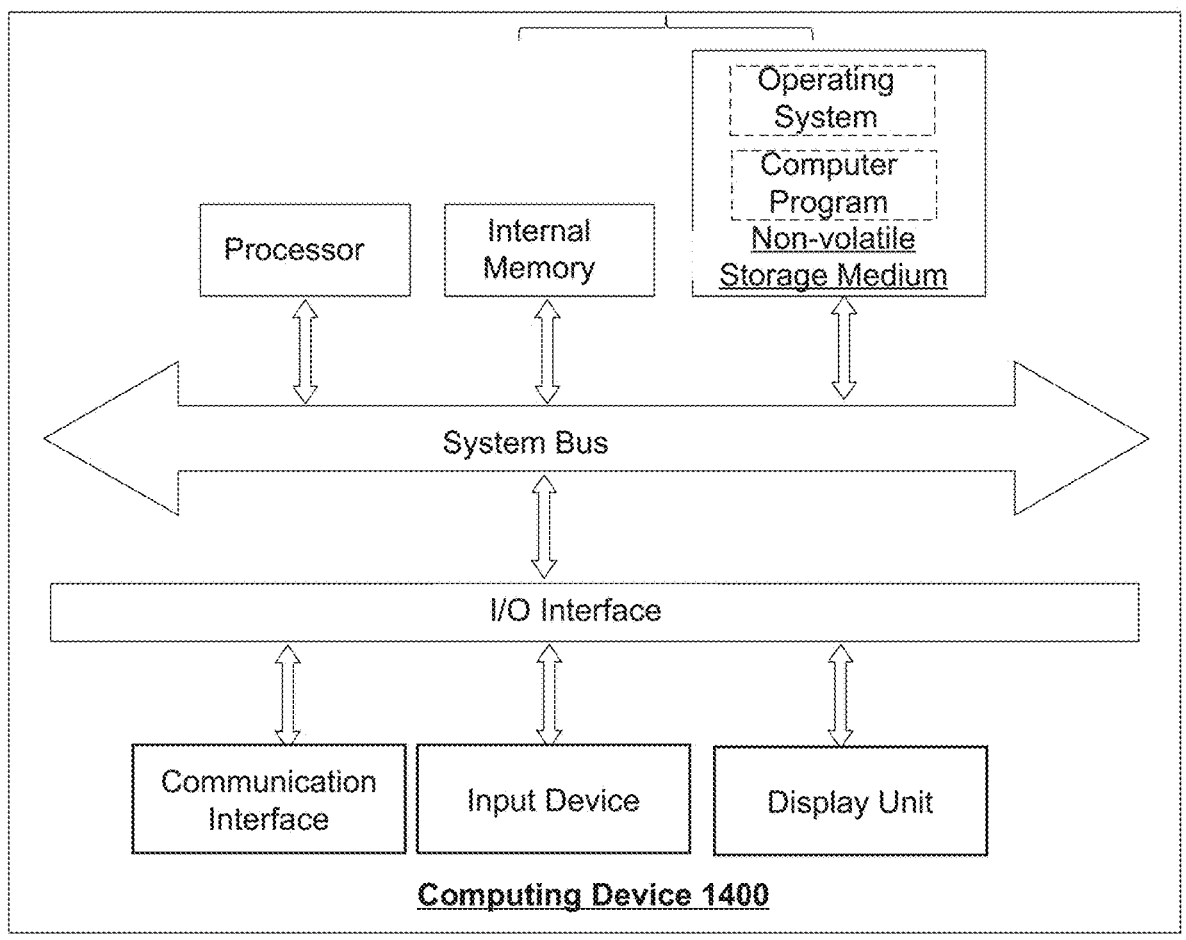
FIG. 14 is a schematic diagram illustrating an exemplary computing device according to some embodiments of the present disclosure.

FIG. 14 is a schematic diagram illustrating an exemplary computing device 1400 according to some embodiments of the present disclosure.

In some embodiments, one or more components of the X-ray imaging system 100 may be implemented on the computing device 1400. For example, a processing engine may be implemented on the computing device 1400 and configured to implement the functions and/or methods disclosed in the present disclosure.

The computing device 1400 may include any components used to implement the X-ray imaging system 100 described in the present disclosure. For example, the processing device 140 may be implemented through hardware, software program, firmware, or any combination thereof, on the computing device 1400. For illustration purposes, only one computer is described in FIG. 14, but computing functions related to the X-ray imaging system 100 described in the present disclosure may be implemented in a distributed fashion by a group of similar platforms to spread the processing load of the X-ray imaging system 100.

The computing device 1400 may include a communication port connected to a network to achieve data communication. The computing device 1400 may include a processor (e.g., a central processing unit (CPU)), a memory, a communication interface, a display unit, and an input device connected by a system bus. The processor of the computing device 1400 may be used to provide computing and control capabilities. The memory of the computing device 1400 may include a non-volatile storage medium, an internal memory. The non-volatile storage medium may store an operating system and a computer program. The internal memory may provide an environment for the execution of the operating system and the computer program in the non-volatile storage medium. The communication interface of the computing device 1400 may be used for wired or wireless communication with an external terminal. The wireless communication may be realized through Wi-Fi, a mobile cellular network, a near field communication (NFC), etc. When the computer program is executed by the processor, a method for determining feature points may be implemented. The display unit of the computing device 1400 may include a liquid crystal display screen or an electronic ink display screen. The input device of the computing device 1400 may include a touch layer covered on the display unit, a device (e.g., a button, a trackball, a touchpad, etc.) set on the housing of the computing device 1400, an external keyboard, an external trackpad, an external mouse, etc.

Merely for illustration, only one processor is described in FIG. 14. However, it should be noted that the computing device 1400 in the present disclosure may also include multiple processors. Thus operations and/or method steps that are performed by one processor as described in the present disclosure may also be jointly or separately performed by the multiple processors. For example, if the processor of the computing device 1400 in the present disclosure executes both operation A and operation B, it should be understood that operation A and operation B may also be performed by two or more different processors jointly or separately (e.g., a first processor executes operation A and a second processor executes operation B, or the first and second processors jointly execute operations A and B).

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended for those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this disclosure are not necessarily all referring to the same embodiment. Furthermore, the particular features, structures, or characteristics may be combined as suitable in one or more embodiments of the present disclosure.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
at least one storage device storing a set of instructions for X-ray imaging; and
at least one processor configured to communicate with the at least one storage device, wherein when executing the set of instructions, the at least one processor is configured to direct the system to perform operations including:
obtaining pre-scan imaging data relating to a target section of a target subject, the pre-scan imaging data being collected by a detector of an X-ray imaging device in a pre-scan, and the target section being irradiated by pre-scan radiation rays emitted by a radiation source located at a fixed location during the pre-scan;

determining, based on the pre-scan imaging data, a chord length of at least one chord of the target section, an extension line of each of the at least one chord passing through a focal spot of the radiation source and a detector position of the detector;
determining, based on the chord length of the at least one chord of the target section, exposure parameters to be used by the X-ray imaging device in a target scan of the target subject; and
reconstructing a target image of the target subject based on scan data collected by the X-ray imaging device in the target scan, the target scan being performed according to the exposure parameters.

2. The system of claim 1, wherein the determining, based on the pre-scan imaging data, a chord length of at least one chord of the target section comprises:
for each of the at least one chord of the target section,
determining, based on the pre-scan imaging data, a first signal intensity detected by the detector position corresponding to the chord;
determining a first distance between the focal spot and the detector position corresponding to the chord and a second distance between the focal spot and a ray exit port of the radiation source; and
determining the chord length of the chord based on the first signal intensity, the first distance, and the second distance.

3. The system of claim 2, wherein the determining the chord length of the chord based on the first signal intensity, the first distance, and the second distance comprises:
determining a second signal intensity at the ray exit port of the radiation source; and
determining the chord length of the chord based on the first signal intensity, the second signal intensity, the first distance, and the second distance.

4. The system of claim 1, wherein the determining, based on the chord length of the at least one chord of the target section, exposure parameters to be used in a target scan of the target subject comprises:
determining, based on the chord length of the at least one chord of the target section, lengths of a major semi-axis and a minor semi-axis of the target section; and
determining, based on the lengths of the major semi-axis and the minor semi-axis of the target section, the exposure parameters.

5. The system of claim 4, wherein the at least one chord includes a first chord and a second chord, the first chord passes through a center of the target section, the second chord does not pass through the center of the target section, and
the determining, based on the chord length of the at least one chord of the target section, lengths of a major semi-axis and a minor semi-axis of the target section comprises:
determining a first function relating to the lengths of the major semi-axis and the minor semi-axis based on the chord length of the first chord;
determining a second function relating to the lengths of the major semi-axis and the minor semi-axis based on the chord length of the second chord;
determining the lengths of the major semi-axis and the minor semi-axis of the target section by solving the first function and the second function.

6. The system of claim 5, wherein
when the first chord is perpendicular to the detector, the first function is determined based on the chord length of the first chord and an orientation of the first chord, when the first chord is not perpendicular to the detector, the first function is determined by:

determining a reference chord that is perpendicular to the detector;

determining a reference distance between the detector position corresponding to the first chord and a detector position corresponding to the reference chord; and determining the first function based on the chord length of the first chord, the reference distance, and an orientation of the reference chord.

7. The system of claim 4, wherein the whole target section is within a field of view of the pre-scan, and the determining, based on the chord length of the at least one chord of the target section, lengths of a major semi-axis and a minor semi-axis of the target section comprises:

dividing the target section into sub-regions based on the at least one chord;

determining areas of the sub-regions based on at least part of the chord length of the at least one chord; and determining the lengths of the major semi-axis and the minor semi-axis of the target section based on the areas of the sub-regions.

8. The system of claim 4, wherein part of the target section is out of a field of view of the pre-scan, the at least one chord includes a first chord passing through a center of the target section, and the determining, based on the chord length of at least one chord of the target section, lengths of a major semi-axis and a minor semi-axis of the target section comprises:

determining a first function relating to the lengths of the major semi-axis and the minor semi-axis based on the chord length of the first chord;

determining a third function relating to the lengths of the major semi-axis and the minor semi-axis based on a tangent line of the part of the target section; and determining the lengths of the major semi-axis and the minor semi-axis of the target section by solving the first function and the third function.

9. The system of claim 4, wherein the determining, based on the lengths of the major semi-axis and the minor semi-axis of the target section, the exposure parameters comprises:

obtaining reference lengths of the major semi-axis and the minor semi-axis of the target section;

determining whether the pre-scan needs to be reperformed based on the lengths and the reference lengths of the major semi-axis and the minor semi-axis of the target section;

in response to determining that the pre-scan needs to be reperformed, obtaining second pre-scan imaging data by performing a second pre-scan on the target section; and determining the exposure parameters based on the second pre-scan imaging data.

10. A method for X-ray imaging, implemented on a computing device having at least one processor and at least one storage device, the method comprising:

obtaining pre-scan imaging data relating to a target section of a target subject, the pre-scan imaging data being collected by a detector of an X-ray imaging device in a pre-scan, and the target section being irradiated by pre-scan radiation rays emitted by a radiation source located at a fixed location during the pre-scan;

determining, based on the pre-scan imaging data, a chord length of at least one chord of the target section, an extension line of each of the at least one chord passing through a focal spot of the radiation source and a detector position of the detector;

determining, based on the chord length of the at least one chord of the target section, exposure parameters to be used by the X-ray imaging device in a target scan of the target subject; and reconstructing a target image of the target subject based on scan data collected by the X-ray imaging device in the target scan, the target scan being performed according to the exposure parameters.

11. The method of claim 10, wherein the determining, based on the pre-scan imaging data, a chord length of at least one chord of the target section comprises:

for each of the at least one chord of the target section, determining, based on the pre-scan imaging data, a first signal intensity detected by the detector position corresponding to the chord;

determining a first distance between the focal spot and the detector position corresponding to the chord and a second distance between the focal spot and a ray exit port of the radiation source; and determining the chord length of the chord based on the first signal intensity, the first distance, and the second distance.

12. The method of claim 11, wherein the determining the chord length of the chord based on the first signal intensity, the first distance, and the second distance comprises:

determining a second signal intensity at the ray exit port of the radiation source; and determining the chord length of the chord based on the first signal intensity, the second signal intensity, the first distance, and the second distance.

13. The method of claim 10, wherein the determining, based on the chord length of the at least one chord of the target section, exposure parameters to be used in a target scan of the target subject comprises:

determining, based on the chord length of the at least one chord of the target section, lengths of a major semi-axis and a minor semi-axis of the target section; and determining, based on the lengths of the major semi-axis and the minor semi-axis of the target section, the exposure parameters.

14. The method of claim 13, wherein the at least one chord includes a first chord and a second chord, the first chord passes through a center of the target section, the second chord does not pass through the center of the target section, and the determining, based on the chord length of the at least one chord of the target section, lengths of a major semi-axis and a minor semi-axis of the target section comprises:

determining a first function relating to the lengths of the major semi-axis and the minor semi-axis based on the chord length of the first chord;

determining a second function relating to the lengths of the major semi-axis and the minor semi-axis based on the chord length of the second chord;

determining the lengths of the major semi-axis and the minor semi-axis of the target section by solving the first function and the second function.

15. The method of claim 14, wherein when the first chord is perpendicular to the detector, the first function is determined based on the chord length of the first chord and an orientation of the first chord, when the first chord is not perpendicular to the detector, the first function is determined by:

determining a reference chord that is perpendicular to the detector;

determining a reference distance between the detector position corresponding to the first chord and a detector position corresponding to the reference chord; and determining the first function based on the chord length of the first chord, the reference distance, and an orientation of the reference chord.

16. The method of claim 13, wherein the whole target section is within a field of view of the pre-scan, and the determining, based on the chord length of the at least one chord of the target section, lengths of a major semi-axis and a minor semi-axis of the target section comprises:

dividing the target section into sub-regions based on the at least one chord;

determining areas of the sub-regions based on at least part of the chord length of the at least one chord; and determining the lengths of the major semi-axis and the minor semi-axis of the target section based on the areas of the sub-regions.

17. The method of claim 13, wherein part of the target section is out of a field of view of the pre-scan, the at least one chord includes a first chord passing through a center of the target section, and the determining, based on the chord length of at least one chord of the target section, lengths of a major semi-axis and a minor semi-axis of the target section comprises:

determining a first function relating to the lengths of the major semi-axis and the minor semi-axis based on the chord length of the first chord;

determining a third function relating to the lengths of the major semi-axis and the minor semi-axis based on a tangent line of the part of the target section; and determining the lengths of the major semi-axis and the minor semi-axis of the target section by solving the first function and the third function.

18. The method of claim 13, wherein the determining, based on the lengths of the major semi-axis and the minor semi-axis of the target section, the exposure parameters comprises:

obtaining reference lengths of the major semi-axis and the minor semi-axis of the target section;

determining whether the pre-scan needs to be reperformed based on the lengths and the reference lengths of the major semi-axis and the minor semi-axis of the target section;

in response to determining that the pre-scan needs to be reperformed, obtaining second pre-scan imaging data by performing a second pre-scan on the target section; and determining the exposure parameters based on the second pre-scan imaging data.

19. A non-transitory computer readable medium, comprising executable instructions that, when executed by at least one processor, direct the at least one processor to perform a method, the method comprising:

obtaining pre-scan imaging data relating to a target section of a target subject, the pre-scan imaging data being collected by a detector of an X-ray imaging device in a pre-scan, and the target section being irradiated by pre-scan radiation rays emitted by a radiation source located at a fixed location during the pre-scan;

determining, based on the pre-scan imaging data, a chord length of at least one chord of the target section, an extension line of each of the at least one chord passing through a focal spot of the radiation source and a detector position of the detector;

determining, based on the chord length of the at least one chord of the target section, exposure parameters to be used by the X-ray imaging device in a target scan of the target subject; and reconstructing a target image of the target subject based on scan data collected by the X-ray imaging device in the target scan, the target scan being performed according to the exposure parameters.

20. The non-transitory computer readable medium of claim 19, wherein the determining, based on the chord length of the at least one chord of the target section, exposure parameters to be used in a target scan of the target subject comprises:

determining, based on the chord length of the at least one chord of the target section, lengths of a major semi-axis and a minor semi-axis of the target section; and determining, based on the lengths of the major semi-axis and the minor semi-axis of the target section, the exposure parameters.

* * * * *